(12) United States Patent
Blainey et al.

(10) Patent No.: US 10,982,289 B2
(45) Date of Patent: Apr. 20, 2021

(54) HYBRIDIZATION PROBES AND USES THEREOF

(71) Applicants: THE BROAD INSTITUTE INC., Cambridge, MA (US); MASSACHUSETTS INSTITUTE OF TECHNOLOGY, Cambridge, MA (US)

(72) Inventors: Paul Blainey, Cambridge, MA (US); Jacob de Riba Borrajo, Petaluma, CA (US)

(73) Assignees: The Broad Institute Inc., Cambridge, MA (US); Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 14/848,976

(22) Filed: Sep. 9, 2015

(65) Prior Publication Data

US 2016/0083783 A1 Mar. 24, 2016

Related U.S. Application Data

(63) Continuation-in-part of application No. PCT/US2014/030415, filed on Mar. 17, 2014.

(60) Provisional application No. 61/786,931, filed on Mar. 15, 2013.

(51) Int. Cl.

| C07H 21/00 | (2006.01) |
| C12Q 1/68 | (2018.01) |
| C12Q 1/689 | (2018.01) |
| C12Q 1/6816 | (2018.01) |
| G01N 21/64 | (2006.01) |
| G01N 21/78 | (2006.01) |

(52) U.S. Cl.
CPC ............ *C12Q 1/689* (2013.01); *C07H 21/00* (2013.01); *C12Q 1/6816* (2013.01); *G01N 21/6428* (2013.01); *G01N 21/78* (2013.01); *C12Q 2600/158* (2013.01); *G01N 2021/6439* (2013.01); *G01N 2201/062* (2013.01); *Y02A 50/30* (2018.01)

(58) Field of Classification Search
CPC ............ C07H 21/00; C12P 19/34; C12Q 1/68
See application file for complete search history.

(56) References Cited

U.S. PATENT DOCUMENTS

| 5,424,413 A * | 6/1995 | Hogan | C12N 15/1068 435/6.1 |
| 5,437,977 A * | 8/1995 | Segev | C12Q 1/6813 435/6.12 |
| 5,948,897 A * | 9/1999 | Sen | C12N 15/10 435/6.12 |
| 6,451,588 B1 * | 9/2002 | Egholm | C12Q 1/6818 435/287.1 |
| 8,877,438 B2 * | 11/2014 | Yin | B82Y 30/00 435/6.1 |
| 9,315,536 B2 * | 4/2016 | Crea | C07H 21/00 |
| 2002/0009738 A1 * | 1/2002 | Houghton | C12Q 1/6809 435/6.16 |
| 2003/0129611 A1 * | 7/2003 | Bao | C12Q 1/6818 435/6.11 |
| 2003/0154033 A1 * | 8/2003 | Yang | C12Q 1/6827 702/20 |
| 2003/0170613 A1 * | 9/2003 | Straus | B82Y 20/00 435/5 |
| 2007/0048759 A1 * | 3/2007 | Luo | C12Q 2525/313 435/6.19 |
| 2010/0285469 A1 * | 11/2010 | Su | C12N 15/1013 435/6.13 |
| 2011/0097716 A1 * | 4/2011 | Natt | C12Q 1/6851 435/6.11 |
| 2011/0212540 A1 | 9/2011 | Yeh et al. | |
| 2011/0223676 A1 | 9/2011 | Krishnan et al. | |
| 2012/0258479 A1 * | 10/2012 | Ding | G01N 21/76 435/7.92 |
| 2018/0092997 A1 * | 4/2018 | Guo | C12N 15/113 |

OTHER PUBLICATIONS

Chakraborty et al., Nucleic Acids Research 37(9) : 2810 (2009).*
Martinez, J. Science 321 :365(2008).*
Odom et al., Nucleic Acids Research 29 (10) :2026(2001).*
Richards et al., JACS 130:5038 (2008).*
Rothemund Nature 440 : 297 (2006) . . . .*
Sarkar et al.,Nucleic Acids Research 33 (01) :143 (2005) . . . .*
Unemo et al., Antimicrobial Agents and Chemotherapy 57 (2) :1057 (Feb. 2013.*
Utaida et al., Microbiology 149 :2719 (2003).*
Yang et al., Analytical Chemistry 83 :6935 (2011).*
Li et al. IEEE Transactions on Biomedical Engineering 55(5) : 1560 (Year: 2008).*
Richter et al. Advanced Materials 12(7) :507 (Year: 2000).*
Aldaye et al. Science 321 : 1795 (Year: 2008).*
Assenberg et al. Nucleic Acids Research 30 (23) : 5142 (Year: 2002).*
Li et al., Controlled assembly of dendrimer-like DNA. Nature Materials 3 : 38 (Year: 2004).*
Roh et al., Engineering DNA-based functional materials. Chem. Soc. Rev. 40:5730 (Year: 2011).*
Hohng et al., Conformational flexibility of four-way junctions. J. of Molecular Biology 336:69-79 (Year: 2004).*

(Continued)

*Primary Examiner* — Ethan C Whisenant
(74) *Attorney, Agent, or Firm* — Melissa Hunter-Ensor; Nicholas R. Bailor; Greenberg Traurig, LLP

(57) ABSTRACT

The present invention relates to novel hybridization probes useful for rapid hybridization to realize a practicable and affordable pathogen diagnostic based on RNA signature detection, technology and hardware. In particular, the present invention relates to a nucleic acid structure which may comprise nucleic acid tiles, wherein each nucleic acid tile comprises nucleic acid oligomers, wherein each nucleic acid oligomer hybridizes to each other thereby forming a nucleic acid tile.

18 Claims, 15 Drawing Sheets

(56) References Cited

OTHER PUBLICATIONS

Li et al. Controlled assembly of dendrimer-like DNA. Nature Materials 3 : 38-42 (Year: 2004).*
International Preliminary Report on Patentability and Written Opinion dated Sep. 24, 2015, which issued during prosecution of International Application No. PCT/US2014/030415.

* cited by examiner

A

Amplification and/or enzymatic processing

| Readout method | | (+) sensitive to enzyme inhibitors, contamination-prone | (−) robust to enzyme inhibition |
|---|---|---|---|
| Sequencing (complex process) | | RT-PCR & sequencing | NONE (amplification-free seq. workflows require enzyme/protein function in some steps) |
| Hybridization (simple process) | | Luminex X-Tag, microarrays, RT-digital QPCR | Nanostring and DNA origami-based detection |

B

| | Nanostring | vision |
|---|---|---|
| instrumentation cost | ~$235,000 | < $50,000 |
| hybridization reaction volume | 30,000 nL | 100 nL |
| cost/patient sample (11 assays) | > $400 | disposable chip: $1 - $60 reagents: < $1 |
| time/patient sample (11 assays) | 16 hours + | < 4 hours |

FIGS. 1A-1B

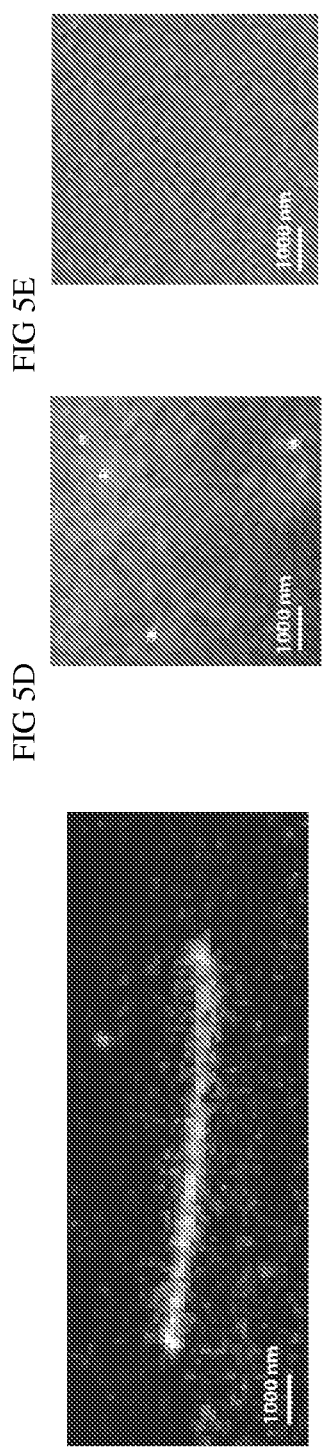
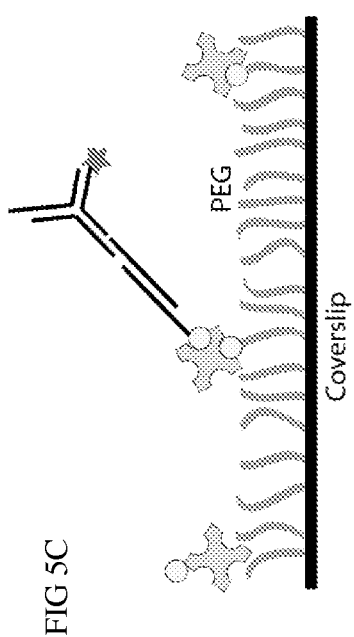
FIG 5A
FIG 5B
FIG 5C
FIG 5D
FIG 5E

HYBRIDIZATION PROBES AND USES THEREOF

INCORPORATION BY REFERENCE

This application is a continuation-in-part of international patent application Serial No. PCT/US2014/030415, filed Mar. 17, 2014, which published as PCT Publication No. WO 2014/145620, on Sep. 18, 2014 and claims benefit of and priority to U.S. provisional patent application Ser. No. 61/786,931 filed Mar. 15, 2013.

The foregoing application, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant no. R21 AI21932 awarded by the National Institutes of Health. The government has rights in the invention.

FIELD OF THE INVENTION

The present invention relates to a novel hybridization probes useful for rapid hybridization to realize a practicable and affordable pathogen diagnostic based on RNA signature detection, technology and hardware.

BACKGROUND OF THE INVENTION

The treatment of routine and life-threatening infectious disease would be revolutionized by a rapid test for pathogen identification and drug sensitivity. The rising incidence of resistance in increasing numbers of strains and the threat of bioterrorism place a premium on universal approaches able to detect previously uncharacterized resistance traits. Culture-based methods for pathogen identification and susceptibility testing are slow (>1 day), labor-intensive, and require many separate measurements to cover a large number of pathogen types and drugs. Rapid, universal identification of pathogen types and drug susceptibilities is a key driver in patient outcomes and epidemic control.

Established concepts for pathogen detection and antibiotic susceptibility in the molecular diagnostics space focus on PCR amplification of genomic loci specific to different classes of organisms or previously characterized resistance mechanisms. This approach is hampered by the amplification reactions required to produce a detectable signal. The need to remove PCR inhibitors from the sample prior to analysis imposes a requirement for nucleic acid purification, adding cost, complexity, and time to the diagnostic process. The amplification process itself requires time and additional reagents, and a large number of assays need to be run in order to cover a large panel of loci reporting on various pathogens and drug resistance markers. Finally, the production of analyze molecules in the course of the assay creates a tremendous potential for contamination and false-positive results. Attempts to address the contamination problem in PCR invariably lead to increased assay cost, greater workflow and instrument complexity, and longer assay times even when contamination-control efforts are successful.

Single-molecule hybridization-based approach, such as NanoString, has several advantages over amplification-dependent methods: 1) High multiplexing capacity that can support the identification and susceptibility profiling of many organisms at once (for a given drug), 2) No need for nucleic acid purification due to the low sensitivity of hybridization reactions to small molecules and proteins present in the sample that can inhibit enzymatic reactions required for nucleic acid amplification, 3) Low susceptibility to contamination from previous assays, as analytes are not amplified in the assay, 4) Excellent sensitivity to low (sub-femtogram) analyte quantities.

Notwithstanding these merits, the specific implementation of NanoString is not suitable for deployment as a clinical diagnostic, as the assay takes too long (~20 hours), requires too many manual steps, lacks sufficient biological resolution for some diagnostic tasks, is not well-suited to interface with the advanced sample preparation methodologies to be developed in subprojects three and five, and requires instrumentation and reagents that are too complex and expensive. While DNA sequencing may be considered as an alternative RNA profiling methodology, current approaches are slow in practice and require PCR amplification or enzymatic modification/processing of the target molecules, suffering as a result the associated drawbacks listed above.

Citation or identification of any document in this application is not an admission that such document is available as prior art to the present invention.

SUMMARY OF THE INVENTION

The present invention relates to a rapid hybridization procedure, new fluorescent hybridization probes, microdevices, and prototype hardware and software to realize a practicable and affordable pathogen diagnostic based on RNA signature detection, technology and hardware. The present invention has applications in biotechnology, from low-cost, rapid, and highly quantitative RNA profiling in eukaryotic cells, to improving hybridization protocols used in targeted sequencing and array-based studies, to novel applications of spectral encoding in single-cell studies utilizing nucleic acid or nucleic acid analog, advantageously DNA origami-based probes.

In particular, the present invention relates to a nucleic acid structure which may comprise nucleic acid tiles, wherein nucleic acid tile comprises one or more nucleic acid oligomers, wherein each nucleic acid oligomer hybridizes to each other thereby forming a nucleic acid tile, wherein each nucleic acid tile comprises two overhangs, wherein the two overhangs are overhangs A and B or overhangs A' and B', wherein A and A' are complementary overhangs and B and B' are complementary overhangs, wherein at least one nucleic acid tile is labeled with a label and wherein the nucleic acid tiles are synthesized by successive addition of nucleic acid tiles hybridizing at overhangs A and A' or B and B' thereby forming the nucleic acid structure comprising nucleic acid tiles.

The present invention also relates to a probe set which may comprise an optical probe which may comprise the nucleic acid structure of the present invention wherein the optical probe may be conjugated to a hybridization probe, wherein the hybridization probe targets a nucleic acid.

The present invention also relates to methods of detecting a target nucleic acid sequence which may comprise adding the probe set of the present invention to a sample which may comprise the target nucleic acid sequence and identifying the target nucleic acid sequence bound to the probe set, wherein the identifying comprises detection of a label.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A-1B depicts technologies for profiling nucleic acid mixtures. A) Categorization of different technology approaches by major assay characteristics. For rapid, sensitive, and reliable assays, the lower right sector representing simple, hybridization-based processes that are not sensitive to enzyme inhibitors is the preferred regime. The Nanostring technology exhibits suitable sensitivity and multiplexing capability for transcription profiling for diagnostics, but currently cannot meet the required specification for assay speed and cost. B) Detail on speed and cost of Nanostring assay versus proposed vision for a DNA origami-based assay. Cost estimates for Nanostring reagents are based on recent quotations from Nanostring for 10,000 100-plex assays. The cost for microdevices at prototype scale is estimated at $60 each (current quoted cost for custom 2-layer devices of the type needed from the Stanford Microfluidics Foundry). Device cost is expected to drop to a few dollars per device for mass production in excess of 10,000 units/year. The estimate for the assay reagent cost is based on list prices and guaranteed yields for HPLC-purified oligonucleotides from Integrated DNA Technologies. At scale, Applicants anticipate the incremental cost per patient sample (inclusive of the disposable microdevice and reagents for 11 assays) to be just a few dollars, allowing the test to be priced competitively versus traditional diagnostic services

FIG. 5A-5E depicts specific recruitment of nucleic acids to surfaces and molecular recognition imaged at the single-molecule level. Lambda DNA molecule specifically bound to a PEG-grafted surface via biotin-streptavidin interaction and stretched by flow of buffer A) schematic B) single-molecule image. C) Schematic showing single-molecule three-way junction tile labeled with a single Cy5 dye molecule hybridized to biotinylated target molecule on surface, D) image of three-way junction tile recognizing target oligo and recruited to surface by biotin-streptavidin as depicted in part C. E) Negative control image with mismatched target oligo demonstrating absence of non-specific binding of probes to poly(ethyleneglycol) surface.

DETAILED DESCRIPTION OF THE INVENTION

Figures 2A, 2B, 2C:
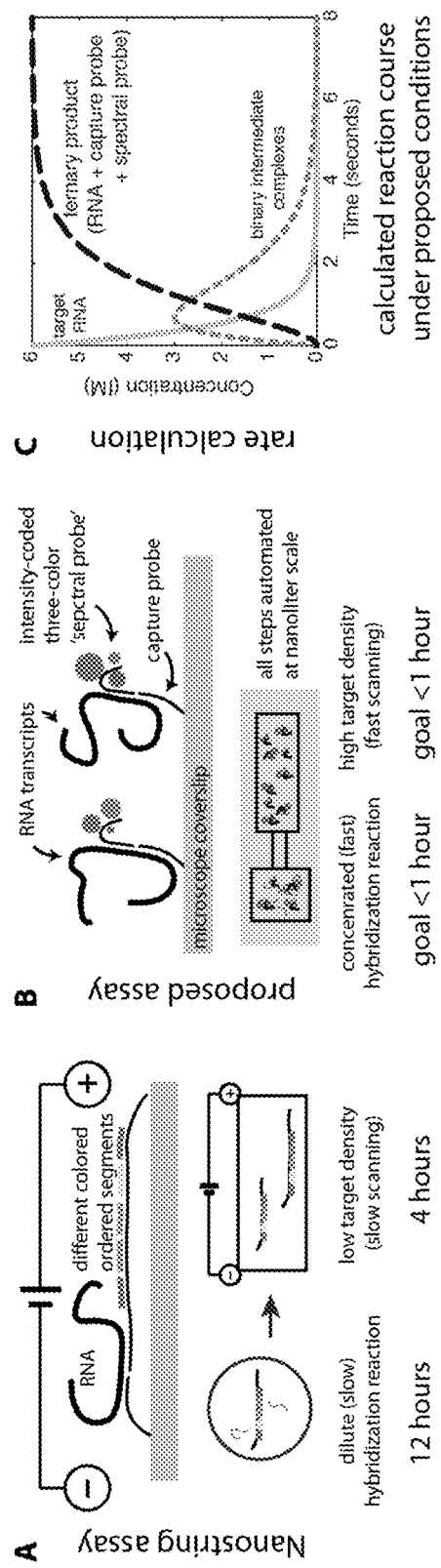
FIG. 2A-2C depicts a schematic of probe arrangement and probe binding reaction in Nanostring and proposed approaches. A) Nanostring assay with stretched probe and order-dependent encoding. B) Proposed assay with encoding in the spectral domain only and rapid hybridization at high target and probe concentration. Total hybridization/deposition+scanning time is 16 hours for Nanostring, and expected at fewer than two hours for the proposed assay. C) Calculated diffusion-limited binding reaction (fundamental upper limit on association rate) between a 6 femtomolar target RNA (~300 target molecules in a 100 nanoliter volume) and capture probes and spectral probes (each probe at 1 micromolar) in solution. The reaction is 80% complete within two seconds, with the ternary complex at a femtomolar concentration. In the Nanostring assay, the target is 300× more dilute and each probe type is estimated to be 10× more dilute, indicating a 3000× lower reaction rate and lower product concentration, limiting in turn the achievable rate of the subsequent surface-recruitment step.

The present invention relates to a microfluidic device for rapid, high-yield hybridization of sub-femtogram quantities of nucleic acid templates with small quantities of nucleic acid-based optical probes. A combination of several methods allow efficient probe-target hybridization in minutes in the context of a microfluidic device to accept crude lysates prepared from clinical samples and deliver probe-target complexes to a surface for high-speed analysis by wide-field optical microscopy. The speed, sensitivity and cost enhancements flow through automation of the sample hand-off, elimination of sample loss, increased probe and target concentration in hybridization reactions through miniaturization, and optimized buffer and thermal conditions during hybridization. The time from sample acquisition to a ready-to image array of probe-target complexes is reduced from ~20 hours by the most closely related commercial method to less than 90 minutes.

The present invention also relates to the design and synthesis of DNA origami-based spectral barcodes; validation of hybridization and co-imaging of spectral barcodes using a wide-field optical microscope. A DNA nanotechnology approach to optical barcoding has many advantages. The present invention encodes multiple brightness levels in up to three color channels to optically barcode hundreds of probes for different mRNA molecules in the spectral domain only (no spatial resolution required within a given barcode). The flexibility of the specific DNA origami approach identified herein facilitates advancements in biological resolution, optical readout speed, and allow simplification of instrumentation needed for readout. In combination with the ready availability of fluorescent oligonucleotides, this is an attractive approach for both early development and deployment at large scale and low cost.

The present invention also relates to a design, building and testing of a microdevice, optical system, and controller capable of counting of >100 nucleic acid target types with 3 decades dynamic range within a few hours or less sample to answer. Applicants are prototyping a series of simplified, low-cost instrumental components capable of executing the RNA targeting assay at high plex and high speed. The fluidic and optical designs realize the speed, sensitivity, and simplification.

The proposed invention develops a proven concept for pathogen identification and susceptibility by RNA profiling that has a strong potential to serve as a universal (many pathogen types, many drug types, de novo-resistance-capable) and rapid platform for pathogen identification and drug susceptibility testing.

The invention is significant because it develops the rapid hybridization procedure, new fluorescent hybridization probes, microdevices, and prototype hardware and software needed to realize a practicable and affordable pathogen diagnostic based on RNA signature detection, technology and hardware that does not exist. The technologies developed herein have important applications in biotechnology more broadly, from low-cost, rapid, and highly quantitative RNA profiling in eukaryotic cells, to improving hybridization protocols used in targeted sequencing and array-based studies, to novel applications of spectral encoding in single-cell studies utilizing the DNA origami-based probes.

The present invention relates to a hybridization-based single RNA molecule counting method that retains the advantages of the NanoString method, but addresses the limitations in speed, cost, and resolution. To do so, six principle advancements need to be realized: 1) the cost of fluorescent hybridization probes needs to be reduced, 2) probe hybridization needs to be driven faster under conditions that require more specific probe-sequence interaction, 3) optical barcodes that do not require probe stretching are needed to allow instrument simplification and higher surface density of targets to allow faster readout, 4) brighter probes needed to further simplify the instrumentation and accelerate probe readout by reducing the required optical sensitivity, 5) low-volume input interface to accept concentrated lysates delivered by technologies developed in subproject five, and 6) potential for processing larger numbers of samples in parallel. Applicant believes these objectives are met by the application of DNA-origami based multi-level fluorescent hybridization probes combined with the samples in a microfluidic format.

Probe hybridization is the slowest step in the NanoString nCounter protocol (16 hours). Fundamentally, there is no limit on the rate of probe hybridization, which can be improved by simply increasing analyte and probe concentrations, and improving hybridization reaction efficiency on a per-probe-target-encounter basis (although care must be taken to avoid introducing kinetic biases). The present invention relates to accelerating probe-target hybridization reactions within the constraints imposed by lysate formatting, probe cost, and hybridization specificity requirements. In short, scaling hybridization reactions from the microliter scale to the nanoliter scale while carefully controlling the reaction conditions has a potential to accelerate hybridization by increasing probe and template concentrations and per-encounter hybridization efficiency while controlling the quantity (cost) of fluorescent probes consumed.

The nucleic acid-origami based assay takes advantage of distinguishable fluorescence intensities across three color channels, obviating any need to resolve the order of the probe signals and allowing a higher surface-density of probe-target complexes. The purely spectral encoding (no spatial component), higher surface density, and higher brightness per channel allows the use of a simpler, lower-cost optical system for readout and faster scan speeds.

This invention is innovative because it translates physical chemistry concepts, microfluidics, DNA nanotechnology, and single-molecule fluorescence imaging to nucleic acid detection in new ways to surpass the limitations of the best current technology (NanoString Ncounter) and meet key objectives necessary to the development of a practical, affordable, next-generation diagnostic platform based on pathogen RNA profiling.

Nucleic acid hybridization exhibits extremely high sequence-specificity under the right conditions. Fundamentally, this is due to coupling between the interactions of different base-pairs, which gives rise to cooperativity and sharp transitions between bound and unbound states, for example, as a function of temperature. Mismatched base pairs can severely disrupt this cooperativity, allowing the likelihood of nonspecific hybridization interactions to be extremely low under conditions that strongly favor fully specific hybridization interactions. The cooperativity of hybridization reactions between nucleic acids is extremely useful to many biotechnologies common today, including PCR, microarrays, fluorescence in situ hybridization, DNA sequencing, the NanoString assay, and more. Hybridization reactions are well-understood from a thermodynamic point of view, and as such, suited to systematic engineering. Another attractive property of DNA hybridization is that it is generally insensitive to interference from small molecules and proteins in solution, and furthermore, that any minor interference is typically sequence-nonspecific, affecting sequence-specific and sequence nonspecific nucleic acid interactions equally.

The present invention relates to a combination of several methods to allow efficient probe-target hybridization in minutes. While the Smoluchowski rate for probe-target interaction indicates rapid hybridization kinetics are possible, hybridization reactions are slowed by entropic barriers for nucleation that are large at high temperature, while enthalpic barriers that are large at low temperature. The magnitudes of enthalpic barriers are strong functions of the target and probe sequences, leading to a distribution of optimum hybridization temperatures in any multiplexed hybridization assay. Bimolecular association rates are the product of two factors: a collision rate between the interacting partners, and a per-collision binding efficiency. The collision rate is a function of the concentration of the molecules, and an inverse function of the size of the molecules. For the highest collision rate, one desires small, fast-diffusing partners at high concentration.

Several measures are taken to maximize the RNA analyte concentration in the hybridization. First, pre-assay analyte loss is minimized by inhibiting hydrolysis of the RNA and adsorption to surfaces, while dilution of the RNA are carefully limited. An integrated microfluidic system is designed to accept concentrated lysate pre-treated with proteinase K and RNAse inhibitors to minimize RNA degradation by RNAse activity and prevent protein-dependent adsorption to surfaces. Proteinase activity is enhanced and surface adsorption of RNA is further minimized by the inclusion of appropriate surfactants (tween, pluronic, lower amounts of SDS) and maintaining a modest buffer ionic strength to screen RNA-surface electrostatic interactions. The integrated microfluidic system eliminates sample loss from dead volumes as well as incomplete pick-up and blow-out effects that are common in pipetting steps.

Although the rate of surface interaction increases as the container volume shrinks and the solute concentration rises (rate goes as 1/V), nucleic acid adsorption may be controlled by surfactants, and the rapid processing enabled here significantly reduces incubation time, hence the risk for adsorption.

One of the lowest-yield steps in many nucleic acid preparation procedures is nucleic acid purification. Because the assay of the present invention does not require purification, this step may be eliminated as well as the associated delay and sample loss associated with it.

Lysis is carried out on a sample of pathogen cells pre-concentrated to $10^3$-$10^6$ cells per microliter. A volume of concentrated lysate of 10-100 nL is transferred to a hybridization reactor with minimal dilution, yielding an analyte concentration increase of about 1000-fold vis-à-vis nanostring. This low hybridization reaction volume (~100 nL) allows the economical application of high probe concentrations to drive the RNA-probe collision rate. For example, applying 100 different probes at a concentration of 1 micromolar each in this volume would require only 1 picomole of probe in total.

Once the RNA targets and probes are combined in the hybridization reactor, each at high concentration, they may be driven to interact at the highest rate by active microfluidic mixing, and increasing diffusion coefficients and reducing the solution viscosity by raising the temperature to within 10 degrees of the probe Tm, to approximately 45 degrees C. New probe sequences may be fully-complementary 18-30 mers rather than 50 mers designed for stability under hybridization when >85% target-complementary.

The present invention also relates to methods of detecting a target nucleic acid sequence which may comprise adding the probe set of the present invention to a sample which may comprise the target nucleic acid sequence and identifying the target nucleic acid sequence bound to the probe set, wherein the identifying may comprise detection of a label, such as a dye molecule. The label or group of labels may be identified by intensity, color, fluorescence lifetime, intensity variation, energy transfer, or photon statistics arising from photophysics of the labels.

A present invention also relates to a method of detecting a target nucleic acid sequence which may comprise adding the probe set of the present invention to a sample which may comprise the target nucleic acid sequence and identifying the target nucleic acid sequence bound to the probe set, wherein the identifying may comprise detection of a label. In an advantageous embodiment, detection of a label may comprise measuring the intensity of the label. The probe set is engineered to be specific to the target nucleic acid. Such methods are known to one of skill in the art.

The preceding paragraphs describe the marshaling of the highest possible concentration of RNA targets and probes into the hybridization reactor, and allowing them to encounter one another. The second factor driving bimolecular association rates is the per-collision hybridization efficiency, which faces entropic barriers at high temperatures, and sequence-dependent enthalpic barriers at lower temperatures for interactions where the probe and/or target contain internal or cross-hybridization structure. Given the need to address many targets simultaneously within the constraints of biological sequence space, it is necessary to presume some internal and cross-hybridization structure among the probes and targets. Applicant efficiently captures all the hybridization interactions by thermally annealing from the ~45 C incubation temperature, where even the stronger internal and cross-hybridization structures re destabilized and able to form the desired specific probe-target hybridized structures rapidly, overcoming the enthalpic barrier associated with internal or cross-hybridization structures. By ramping down the temperature during the hybridization reaction, Applicant captures properly formed probe-target structures while accelerating yet-unformed interactions by reducing the temperature-dependent entropic nucleation barrier to hybridization as the final temperature is approached, 25 C. All the intended fully-complementary hybridization interactions are stable at 25 C, while the probe set are already been screened against the database of pathogen sequences to eliminate those with stable sequence-nonspecific interactions. Since the assay requires hybridization of both the fluorescent spectral probe and the capture probe to produce a signal, the probability of producing a false-positive signal is much lower than assays dependent on the hybridization of a single probe, specifically, if the probability of a single nonspecific probe-target interaction is some small number p, the probability of a spectral probe-target interaction and a nonspecific capture probe-target interaction on the same target molecule (required for production of a false-positive count) is $p^2$, some very small number. Thermal annealing is commonly used to achieve rapid and specific annealing of oligonucleotides to single-stranded targets (eg in transition from the melting step to the priming step in PCR), but is not specified in the protocol for some hybridization reactions in targeted sequencing or the NanoString nCounter procedures.

FIG. 2 shows the steps involved in the proposed assay, which is similar to the NanoString nCounter workflow, with key differences that all steps are integrated into a single automated microfluidic device optimized to accept a nano-liter volume of concentrated lysate from the sample prep modules. Specifically, this includes a ring-shaped chamber with partitions into which lysate, reporter probe mix, capture probe mix, and diluent can be metered and mixed by microfabricated pumps. For initial testing, the entire device sits on a flat-top PCR thermocycler for easy testing of different temperature profiles. Subsequently, a valve opens allowing the sample to flow into and be cycled through an imaging region where the biotinylated capture probes (both free and in complex with targets and reporter probes) bind the streptavidin-coated lower surface of the imaging region. Here there is a dual advantage over the NanoString flow cell configuration that lends 1) speed and 2) sensitivity advantages. The 100-1000-fold higher concentration of probe-target complexes in the proposed assay increases the surface binding rate by the same factor, with the dividend freely chosen to apportion across the speed-yield tradeoff. Secondly, although NanoString procedure prepares 30 microliters of lysate, fewer than 10 microliters are loaded in the imaging flow cell, and the volume of the imaging area is only ~1 microliter, meaning only $\frac{1}{30}^{th}$ of the sample has the opportunity to efficiently bind the flow cell surface. Because the entire hybridization reaction is introduced to the imaging area in the proposed assay, a 30× improvement in sensitivity is expected independent of any improvement in yield gained from the higher target complex concentration.

After surface capture, the imaging area is flushed with a controlled flow of hybridization buffer to remove excess probes, non-target RNA and other cellular components. At this point, a slow flow of hybridization buffer is applied for a controlled time and temperature to allow kinetically unstable non-specific complexes to be disrupted and flushed away. The remaining stable probe-target complexes are then ready for imaging with low fluorescence background. In initial testing, this imaging is carried out on a commercial inverted fluorescence microscope equipped with an LED epifluorescence illuminator and scientific-grade detector.

To assess the impact of concentration, annealing protocol, and different surfactants on hybridization rate and yield, time-dependent measurements of probe-target complex density as functions of probe concentration, annealing rate/time, buffer composition, and surface capture time is made. Initially, the template is purified total RNA and three mRNA simple hybridization probes are labeled three color channels. By targeting two singly-labeled probes per RNA transcript and assessing the distribution of probe labels per target by photobleaching analysis as a function of hybridization reaction time, Applicant can deconvolude hybridization efficiency from probe labeling efficiency, which are both key performance criteria that bear on detailed assay design choices. Next, the same rate/yield analysis is carried out in partnership with subproject 5 on crude lysates of concentrations corresponding to $10^2$, $10^4$, and $10^6$ bacteria per microliter to determine the effect of cellular components on the hybridization reaction. Finally, the rate/yield analysis is applied in to crude lysates from clinical samples.

If RNA is degraded in the chip, the stringency of protease treatment of the lysate is increased, include an RNAse inhibitor cocktail, chelators to remove divalent metal cofactors, and the device is treated to destroy any RNAse by UV irradiation and hypochlorite rinse prior to substrate bonding. RNAse activity can be detected by lower-than expected counts in the test with calibrated input of purified RNA and confirmed by degradation of a run-off transcript of known length to lower molecular weight incubated in the device in a mock RNA quantification experiment.

If solution hybridization does not meet a goal of 50% yield for 0.2 fg of a given target transcript in less than 1 hour based on the strategies described above, there are additional measures that may be taken. The effective concentration of nucleic acids may be increased by adding low molecular weight glycols to crowd the solution. The electrostatic repulsion between binding partners may be reduced by increasing ionic strength (particularly divalent cations), by linking the probe to a positively charged or eliminated by introducing a peptide nucleic acid (PNA) probe chemistry with a neutrally-charged amide-linked backbone. If an entropic barrier to hybridization is suspected (slow hybridization of structure-free probes at higher temperatures), a locked nucleic acid (LNA) base may be incorporated in the probe to pre-organize the probe for hybridization and reduce the entropic nucleation barrier. If enthalpic barriers are suspected (slow hybridization of probes with internal structure at lower temperatures), additives that stabilize single-stranded nucleic acids relative to double-stranded nucleic acids such as DMSO or $E$ $coli$ single-stranded binding protein can be employed, and efforts to avoid probe and target internal structure and cross-reactivity can be redoubled If surface capture is does not meet a goal of 50% yield for 0.2 fg RNA input-equivalent input within one hour based on the above approach, the following additional measures are taken. The unreacted capture probes can be depleted by dilution or separation. The geometry of the imaging region may be altered to increase the active surface area to volume ration. Finally, the surface density of streptavidin may be enhanced by loading the streptavidin monolayer with a multiply-biotinylated polymer or structure (DNA-based or synthetic) to which additional streptavidin tetramers may be bound, increasing the number of capture sites and extending some of these into solution to enhance target capture. A related challenge may be that the capture probe concentration required for fast kinetics results in too many unreacted capture probes that swamp binding sites in imaging area, competing with the surface capture of target-hybridized capture probes, despite Applicant's best attempt to design in an excess of capture sites over the total number of capture probes employed in the assay. This case is also ameliorated by several of the measures described to enhance surface capture rates of target-hybridized capture probe, but in addition, a purification step to reduce the number of unreacted capture probes may be employed. This could work by capture of unreacted hybridization probes to beads or a surface in the device by a hybridization interaction prior to passing the probe-target complexes to the imaging region. Alternatively, the capture probes may be pre-loaded on the imaging area surface, and target RNA captured to the surface by a hybridization interaction rather than a biotin-streptavidin interaction.

The present invention is advantageous to bead-based hybridization probes in that the probes of the present invention are significantly smaller than bead-based probes. For example, beads are about $10^{13}$ g/mole, whereas the size of the probes of the present invention are about $10^6$ g/mole.

The present invention also relates to a design and synthesis of nucleic acid origami-based spectral barcode and validation of imaging of nucleic acid origami-based and microdroplet digital PCR-based spectral barcodes using a high performance optical microscope.

The requirement of multiplexing at the scale of hundreds places strong constraints on the design of the RNA-profiling assay. To meet goals of very high probe density on the surface of the imaging region and the ability to image a large region at once, Applicant requires a multiplexing scheme with high signal intensity and encoding only in the spectral domain (no spatial component such as that implemented in the NanoString technology). The currently known approaches are to expand the number of colors, by expanding the spectral range and utilizing emitters with narrower emission spectra such as quantum dots, encoding spatial relationships in the spectral channel, by utilizing fluorescence resonance energy transfer, for example, or by utilizing multiple distinguishable intensity levels in a small number of color channels. The latter approach is selected for this application as the most feasible for meeting project goals.

By encoding n absolute intensity levels in each of m spectral channels, an $n^m$ plex encoding capability is created. For example, if n=six intensity levels are encoded in m=three color channels, $6^3=6\times6\times6=216$-plex capacity is generated. Such schemes have been commercialized for polymer beads, but Applicant is unaware of an application of multi-level encoding at any significant scale at the single-molecule level. This leaves open the question of how to create multi-level probes for the present assay. Probe synthesis must be rather accurate, otherwise the different 'codes' may not be properly distinguished. Applicant favors a structure structure, wherein the number of fluorophores can be encoded deterministically when the structure is being built generation-by-generation by the inclusion of unlabeled monomers or monomers labeled with organic labels in each generation. The deterministic placement of dyes in the structure is key to generating multiple, sharply-defined intensity levels in a small structure containing less than 100 labels in total. The invention encompasses multiple labels, such as 1, 2, 3, 4, 5, 6, 7, 8, 9, 10, 11, 12, 13, 14, 15, 16 17, 18, 19 or 20 labels as well as combinations of different types of labels, such as but not limited to red, green, and blue absorbing/emitting labels.

Such a structure may be constructed by chemical synthesis using one of many synthetic organic structure chemistries that have been demonstrated, or alternatively, using DNA origami technology, a set of methods developed over the last decade (see, e.g., Li et al., Nature Biotechnology Volume 23 Number 7 Jul. 2005 and Li et al., Nature Materials, Vol 3, January 2004). The structure approach has two unique advantages—structures can be constructed step-wise from as few as two distinct modular building blocks (or a single block if a deprotection step is used), limiting the number of starting materials that need be prepared. In addition, the structure approach is flexible, with the number of encoded intensity levels, intensity of the lowest intensity level, and the spacing between intensity levels chosen with some freedom by varying the number of generations in the structure, and the placement of labeled monomers within it.

Although a synthetic structure could be size-efficient and amenable to innumerable variations to engender different properties, novel (e.g., dye-modified) monomers need to be produced, chemistry to link to a hybridization moiety developed, and yields carefully optimized to guarantee distinguishability of the different encoded levels. By contrast, a DNA nanostructured structure is 'natively addressable' to nucleic acid targets, produced cheaply in high yield and high purity by taking advantage of programmed hybridization interactions stabilized by covalent ligation, and dye conjugation can be outsourced to high-quality commercial oligo vendors.

Specifically, Applicant favors the construction of nucleic acid structures based on three-way DNA junctions, where up to 5th generation structures were assembled in high yield without purification. A branched DNA origami structure is better for constructing the needed probes than a linear structure assembled from overlapping oligonucleotides because in the structure, a large number of intensity levels may be encoded in a small number of steps (n coupling steps produces [$2^{(n+1)}-1$] nonzero intensity levels in Applicant's scheme, or $1+3(2^n-1)$ for a three-branch scheme), whereas in a linear structure built step by step, the number of intensity levels created scales only linearly the number of coupling steps.

The nucleic acid structure may comprise nucleic acids or nucleic-acid like molecules, such as but not limited to, DNA, RNA, methylated RNA (such as 2' O-Me RNA), locked nucleic acids (LNA™), and peptide nucleic acids (PNA).

One embodiment of the present invention relates to a DNA structure which may comprise three way junction DNA (sometimes referred to as Y-DNA) tiles (sometimes referred to a monomer), wherein each three way junction DNA tile comprises three DNA oligomers, wherein each DNA oligomer hybridizes to each other thereby forming a three way junction DNA tile, wherein each three way junction DNA tile comprises two overhangs, wherein the two overhangs are overhangs A and B or overhangs A' and B', wherein A and A' are complementary overhangs and B and B' are complementary overhangs, wherein at least one three way junction DNA tile is labeled and wherein the three way junction DNA tiles are synthesized by successive addition of three way junction DNA tiles hybridizing at overhangs A and A' or B and B' thereby forming the DNA structure comprising at least seven three way junction DNA tiles. The present invention also encompasses four way junction DNA tiles and all embodiments discussed herein regarding three way junction DNA tiles also apply to four way junction DNA tiles. Furthermore, all embodiments discussed herein regarding three way junction DNA tiles may be extrapolated to all DNA tiles.

In a first embodiment, one three way junction DNA tile is labeled. In a second embodiment, two three way junction DNA tiles are labeled. In a third embodiment, three way junction DNA tiles are labeled. In a fourth embodiment, four three way junction DNA tiles are labeled. In a fifth embodiment, five three way junction DNA tiles are labeled. In a sixth embodiment, six three way junction DNA tiles are labeled. In a seventh embodiment, seven three way junction DNA tiles are labeled.

In another embodiment, the DNA structure may comprise seven three way junction DNA tiles. In another embodiment, the DNA structure may comprise fifteen three way junction DNA tiles. In another embodiment, the DNA structure may comprise thirty-one three way junction DNA tiles.

The three way junction DNA tile may be labeled with a single label, wherein each DNA structure is distinguishable based upon a varying intensity of the single label. In another embodiment, the three way junction DNA tile may be labeled with two labels wherein each DNA structure is distinguishable based upon a varying intensity of the two labels. In yet another embodiment, the three way junction DNA tile may be labeled with three labels wherein each DNA structure is distinguishable based upon a varying intensity of the three labels.

The smaller number of coupling steps required to produce structureic probes with a given number of encoded levels is critical to the production of a large number of differently encoded probes each in high yield without onerous purification steps. Another advantage of the three-way junction scheme is that up to three dyes per tile can be included using singly-labeled oligonucleotides, since a tile is composed of three oligonucleotides. This approach could be used to make the intensity levels easier to distinguish by increasing the size of the intensity difference between levels (e.g., a spacing of three label units per level). Alternatively or in addition, the spacing between levels may be doubled by creating a structure with one additional generation and deploying tiles in pairs for the purpose of encoding. In any scheme, the lowest few intensity levels may be intentionally left dark to increase the minimum intensity that needs to be detected. This is important both for allowing detection in larger fields of view by simpler, smaller, and less expensive optical systems, but also for a fundamental reason in multi-color applications.

While Applicant can create very high theoretical encoding capacities (46^4=4,477,456 combinations in a fifth generation three-branch scheme in four colors), the ultimate limit on the useful number of levels per color is limited by the spectral cross-talk of the optical detection system. Specifically, the light bleeding from one color channel to another from the highest out-of-channel intensity must be than and distinguishable from the lowest encoded intensity in-channel. Thus, the ability to drop out the lowest few channels relaxes the requirement for optical contrast ratio across the channels. Even without dropping channels, the high-quality optical filters available today and judicious choices of fluorescence excitation and detection bands allow contrast ratios of at least 50×, and the ability to distinguish more than 20 intensity levels per color channel. In fact, the practical limit on the number of distinguishable levels is likely to be driven my mundane considerations such as the illumination intensity uniformity across the imaged area.

In an advantageous embodiment, Applicant assembles third-generation DNA structures from three-way junction tiles where one arm of the seed tile is appended with a single-stranded DNA oligonucleotide designed to hybridize to the target RNA. Such structures consist of a total of seven tiles assembled in two sequential annealing/ligation steps that produce the desired structures in high yield without purification. This structure allows the encoding of up to seven equally-spaced intensity levels, where the intensity interval is three labels per level (located near the three-way junction to avoid interference with the annealing and ligation reactions). Assigning multiple labels per level makes the levels more distinguishable not only by increasing brightness, but also by averaging over stochastic photophysical dynamics of the labels, and providing robustness to a low fraction of source materials lacking an emissive fluorophore. A set of structures encoding seven intensity levels with Cy3 is synthesized and tested in targeting a biotinylated single-stranded DNA target both in solution and when the target is presented on a surface. Applicant resolves the different intensity levels by imaging engineered mixtures of structures encoding different combinations of intensity levels and comparing the calls with the true composition of the mixture. The increase of fluorescence intensity with increasing numbers of labels is calibrated in these experiments. The possibility of getting additional information about the number of labels per target is evaluated by counting steps in a photobleaching trajectory from each probe-target complex. A linear increase in fluorescence with the number of labels in a structure is not a requirement for this assay, in fact sub-linearity may constitute an advantage.

Examples of a label which may be employed include labels known to those skilled in the art, such as fluorescent dyes, enzymes, coenzymes, chemiluminescent substances, and radioactive substances as long as the label detects a double-stranded nucleic acid. Specific examples include radioisotopes (e.g., $^{32}P$, $^{14}C$, $^{125}I$, $^{3}H$, and $^{131}I$), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added. Advantageously, the label intercalates within double-stranded DNA, such as ethidium bromide.

Advantageously, the label is a fluorescent label. The dye may be an Evagreen dye or a ROX dye. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

The label may be a a fluorescent label, advantageously fluorescein or rhodamine. In another embodiment, the label may be an organic label.

Two additional sets of seven differently-labeled structures are advantageously synthesized with Cy5 and Fluorescein (Fluorescein, Cy3, and Cy5 are commercially available as 'internal' oligo modifications) to complete a library of 21 structures encoding seven intensity levels in each of three colors. Combinations of structures from this library yields $7^3=343$-plex multiplexing capacity. To demonstrate this capability, one structure of each color is targeted to synthetic DNA scaffolds targeted in turn to a biotinylated single-stranded DNA target and the most challenging color/intensity combinations tested as described above where structures of a single color were tested. Scripts automating the acquisition of images, and signal identification/counting from many fields of view are developed.

To validate the performance of the probes on mRNA, the same experimental progression described previously are employed (purified RNA, crude lysate from lab cultures, crude lysate from clinical samples), with the exception that the assay is tested in a minimum 100-plex format with probes targeting at least five different pathogenic organisms. These assays include nonspecific probes for which no targets exist (negative controls to assess nonspecific binding) as well as positive-control probes targeting biotinylated DNA targets spiked into the lysate at known concentrations.

A number of contingent responses to uncertainties are prepared. If ligation of the tiles is insufficiently complete, the stem region of the tiles is expanded to space the ligation sites farther from the three-way junctions and fluorophores, and increase the amount of ligase used. Alternatively, the tile-tile interactions are made thermally stable independent of ligation by designing long, GC-rich overlaps between the tiles. If the structures are too sticky for surfaces in the device, DNA hairpins are attached to stabilize the unoccupied tile sites and reduce the number of unpaired bases in the structure. The ionic content and surfactant profile is tuned in the hybridization buffers to prevent nonspecific interaction of the probes with surfaces. The poly(ethylene glycol) graft surfaces used are known to be extremely effective in suppressing the adsorption of both proteins and nucleic acids. Protocols are also available to graft PEG onto PDMS surfaces if the coating of all interior surfaces of is necessary.

If the dead fluorophore content of the oligonucleotides is too high, the oligos are protected from light, high heat, and extreme pH during structure assembly and storage, compete different vendors on this metric, and/or design a larger interval (4, 6, or 8 labels) between each fluorescence intensity level by the approaches described above. The number of active fluorophores on a DNA nanostructure is easily assessed by counting the number of steps to complete photobleaching.

If spectral crosstalk is too high and makes it hard to reliably distinguish the lowest in-band and highest out-of-band intensity levels, the crosstalk is reduced by narrowing and shifting the excitation and emission bandpass regions by changing filters, optionally dropping the lowest intensity level from the encoding scheme, and/or incorporate photobleaching step number data in our classification algorithm.

If the probes are found to be insufficiently specific (perhaps as a consequence of the high-concentration hybridization condition), a number of measures are taken. The final temperature of the hybridization reaction may be increased to disfavor formation of nonspecific complexes. The wash step after binding in the imaging region may be made more stringent by duration, temperature, and by lowering the ionic content. Such stringency may be calibrated by analysis of the retention of control (synthetic) probe-target complexes of varying (known) degrees of thermodynamic and kinetic stability. A final measure to increase specificity is to design the termini of the signal and capture probes to be adjacent, such that they could be ligated after surface capture and a mild wash to remove inhibitors and introduce a ligase. Nonspecific signal and capture-probe interactions on a target are unlikely to be adjacent and be ligated. Post-ligation, a very stringent wash is applied to reverse unligated probe-target interactions, leaving only the designed interactions to remain on the surface for imaging.

The present invention also relates system, and controller capable of counting of 100+ nucleic acid target types with 3 decades dynamic to the design, building, and testing of a simplified microdevice, optical range within 4 hours.

To make an impact on the public in the diagnostics space, the herein invention is translated into a practical (easy-to-use, reliable, low-cost) instrument appropriate for placement in a clinical diagnostics lab at a hospital or community clinic. Future, refined, and possibly more highly targeted versions may address under-resourced settings and point-of-care scenarios.

In order to do so, the present invention reduces the hybridization and imaging steps of the new diagnostic platform to practice on a miniaturized platform constructed from commodity mechanical, electronic, and optical components. Applicant designs and builds such hardware and software to control it, to accept the samples provided by the cell concentration, drug exposure, and lysis modules for probe hybridization and target-probe complex imaging. FIG. 5 shows a schematic of the diagnostic instrument indicating the specific components used in the hybridization and imaging steps and points of contact with the upstream modules.

To the hybridization module is naturally compact and scalable to a large number of samples as a result of the microfluidic miniaturization. The existing reactor/imaging chip is set up to process 24 samples simultaneously, with a strong potential for expansion to greater sample numbers. The main translational needs in prototype development are tight integration with the sample prep modules and miniaturization/cost-engineering the optical system which ensure input/output compatibility and low dead-volume handoffs between the different modules. With respect to the optical subsystem, Applicant designs and builds a custom, compact microscope purpose-built for automated, high-speed imaging of target-probe complexes in the imaging areas of the microfluidic devices.

The diagnostic instrument takes the form of a desktop device approximately the size and weight of a real-time PCR machine. At the front is a tray accepting samples, antibiotics, and the signal/capture probe mixture. Inside is located a microfluidics control module, the cell concentration microdevice, the drug exposure and lysis microdevice, and the hybridization device with an optical system for fluorescence readout.

The optical subsystem requires the most development in the translation from a research breadboard system to the benchtop integrated instrument. The hybridization chip is mounted on a commercially available heating platform for temperature-controlled hybridization and wash steps, then moved in a single linear motion onto a 3d printed receptacle that serves as a microscope stage. This transfer step allows better utilization of the instrument as a second set of samples can undergo hybridization while the first is being imaged.

Above the stage is a light emitting diode array with optically-filtered LEDs in three colors, each of which tuned to excite one of the three colors in the optical barcode. Beneath the stage is located a 20× or 40× air objective on a focusing mount. A two-axis programmable translator with a spatial precision of 50 micron or better allows automatic scanning of the imaging area on the microdevice by moving it with respect to the fixed objective lens. A motorized filter wheel in the emission path includes four positions, one to filter the emission of each color in the optical barcodes, plus a blank position for focus registration on fiducial marks in the sample (microfabricated features or beads randomly scattered in the imaging area) under low-intensity illumination. The light collected by the objective lens is focused on a high-resolution, low noise, low speed, charge-coupled device array image sensor. One long integration time image in the three color channels is recorded from each field of view onto the laptop computer that controls the instrument.

Software controls the fluidics module, stage, focus mount, filter wheel, LED light source, and camera. Probe counts are made by image analysis routines essentially identifying probe-target complexes by image thresholding, and integrating photon counts above background in a neighborhood. The intensity level for each color channel for each target is determined using a previously defined calibration for the probe configuration/buffer condition used, and diagnostic calls made for each sample at the conclusion of the run. These control systems and analysis algorithms sit behind a simple user interface that steps the user through sample and micro-device loading while verifying these steps have taken place by reading microswitch states.

Test samples and standard operating procedures are established for this instrument. A test device with a defined concentration of the three labels employed in the assay spin-coated on the surface is used to verify that the excitation uniformity and the optical crosstalk are within specification across the field of view. A 'test analyte' mixture of synthetic RNA sequences (produced by in vitro synthesis of run-off transcripts) are developed to validate instrument performance, specifically on the hardest-to-distinguish probe combinations.

If sufficiently uniform illumination is difficult to achieve by engineering the LED projection scheme geometry and by adding light-diffusing elements, Applicants alternatively projects the light in a Köhler illumination geometry from a white LED with an additional optical filter wheel on the illumination side, or simply calibrate the instrument to accommodate a systematic variation in illumination intensity recorded using the test sample.

If the images are too noisy with lower-power objective lens, there are a number of measures Applicant may take. First, Applicant moves to an immersion objective with higher numerical aperture to improve the light-gathering power of our system. This is feasible since the hybridization microdevice is formatted on a number 1 glass coverslip, allowing application of the highest-power objective lenses. For example, 20× objective lenses with numerical apertures up to 0.75 are commonly available, and the advantage in field of view, hence scan speed over higher-power 60× or 100× objectives is considerable (9-fold and 25-fold, respectively). Because of the adaptability of our DNA origami based probe design, Applicant has the option of increasing minimum signal intensity and level spacing by altering the probe configuration.

The system, as described in the present technique or any of its components, may be embodied in the form of a computer system. Typical examples of a computer system includes a general-purpose computer, a programmed microprocessor, a micro-controller, a peripheral integrated circuit element, and other devices or arrangements of devices that are capable of implementing the steps that constitute the method of the present technique.

The computer system may comprise a computer, an input device, a display unit and/or the Internet. The computer further comprises a microprocessor. The microprocessor is connected to a communication bus. The computer also includes a memory. The memory may include Random Access Memory (RAM) and Read Only Memory (ROM). The computer system further comprises a storage device. The storage device can be a hard disk drive or a removable storage drive such as a floppy disk drive, optical disk drive, etc. The storage device can also be other similar means for loading computer programs or other instructions into the computer system. The computer system also includes a communication unit. The communication unit allows the computer to connect to other databases and the Internet through an I/O interface. The communication unit allows the transfer as well as reception of data from other databases. The communication unit may include a modem, an Ethernet card, or any similar device which enables the computer system to connect to databases and networks such as LAN, MAN, WAN and the Internet. The computer system facilitates inputs from a user through input device, accessible to the system through I/O interface.

The computer system executes a set of instructions that are stored in one or more storage elements, in order to process input data. The storage elements may also hold data or other information as desired. The storage element may be in the form of an information source or a physical memory element present in the processing machine.

The set of instructions may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing or a request made by another processing machine.

The present invention also encompasses use of the microdevice for extracting nucleic acids from a biological sample, such as a bodily fluid or laboratory sample. The present invention also encompasses use of the microdevice for mixing labeled DNA structures with nucleic acids from the biological sample. The present invention also encompasses use of the microdevice wherein the device mixes the sample and probes in a small volume at high concentration to enable rapid reaction between the probes and sample nucleic acids. The present invention also encompasses use of the microdevice with surface chemistry recruiting probe-conjugated sample nucleic acid molecules to a surface to enable microscopy of the probe-sample molecular conjugates. The present invention also encompasses use of the microdevice for integrating one, two, three, four, or all of the functions as described.

A scheme for self-assembling DNA-based structure nanoprobes that hybridize to specific sequences in target RNA molecules is proposed. Elaborations on a scheme to enable multi-level signal coding (7 non-zero levels in third-generation structures) enables the generation of 343 codes when structures of three colors are combined in a molecular analog to Luminex™ beads. Because these combinations are to be decoded in the spectral domain, there is no requirement to stretch the template or spatially resolve probes.

Existing protocols for high-efficiency hybridization between target molecules and probe molecules specify long incubation times, up to three days. Applicant proposes a combination of several methods to allow efficient probe-target hybridization in minutes. While the Smoluchowski rate for probe-target interaction indicates rapid association is possible, hybridization reactions are slowed by entropic barriers for nucleation that rise with temperature, and enthalpic barriers that fall with temperature. The magnitudes of enthalpic barriers are strong functions of the target and probe sequences, leading to a distribution of optimum hybridization temperatures for a multiplexed hybridization assay. Thermal annealing, which may be applied to small volumes in a microdevice quickly with low applied power, are used to allow each interaction to proceed at its optimum temperature while efficiently capturing the products.

RNA detection is accelerated by streamlining the workflow to require three or fewer day-of-assay bimolecular association steps involving the RNA target: one in-solution hybridization reaction, and one or two solution-to-surface binding steps. Both of these steps are enhanced by limiting the dilution of target RNA molecules during the lysis step to less than 100,000-fold (vis a vis their concentration in cells) and carrying out these bimolecular association reactions in the small volumes that result. In nanoliter or smaller volumes, higher concentrations of probe molecules are afforded for mixing with boosted concentrations of target molecules. This scenario yields a triple benefit under the pseudo-first order kinetic scenario: hybridization yield is accelerated in proportion to the increase in probe concentration, the concentration of product molecules after a time lapse is increased by the product of the increases in probe and target concentrations, and the endpoint yield is enhanced. With respect to surface-binding of target-probe complexes, the low volume allows the entire volume to be incubated in the detection chamber at higher concentration, accelerating the surface-binding reaction in terms of concentration and fractional yield. Kinetically unstable non-specific products are eliminated by a wash of calibrated stringency prior to counting and categorizing surface-bound target complexes.

The application of locked nucleic acid bases, PNA, and multi-partite probes has the potential to further accelerate hybridization reactions. The reduction of hybridization reaction volumes to the nanoliter scale or smaller enables economical application of such 'exotic' probes.

Thermal annealing, which may be applied to small volumes in a microdevice quickly with low applied power, allows each interaction to proceed at its optimum temperature while efficiently capturing the products.

Applicant further accelerates the RNA detection portion of the workflow by streamlining the workflow to require three or fewer day-of-assay bimolecular association steps involving the RNA target: one in-solution hybridization reaction, and one or two solution-to-surface binding steps. Both of these steps may be enhanced by limiting the dilution of target RNA molecules during the lysis step to less than 100,000-fold (vis a vis their concentration in cells) and carrying out these bimolecular association reactions in the small volumes that result. In nanoliter or smaller volumes, higher concentrations of probe molecules may be afforded for mixing with boosted concentrations of target molecules. This scenario yields a triple benefit under the pseudo-first order kinetic scenario: hybridization yield is accelerated in proportion to the increase in probe concentration, the concentration of product molecules after a time lapse is increased by the product of the increases in probe and target concentrations, and the endpoint yield is enhanced. With respect to surface-binding of target-probe complexes, the low volume allows the entire volume to be incubated in the detection chamber at higher concentration, accelerating the surface-binding reaction in terms of concentration and fractional yield. Kinetically unstable non-specific products are eliminated by a wash of calibrated stringency prior to counting and categorizing surface-bound target complexes.

The application of locked nucleic acid bases, PNA, and multi-partite probes have the potential to further accelerate hybridization reactions. The reduction of hybridization reaction volumes to the nanoliter scale or smaller enables economical application of such 'exotic' probes.

Although the preferred embodiment of the present invention is to measure nucleic acids, the invention may also be used to detect a small molecule, a nucleic acid, a peptide, a protein or an analog or derivative thereof. For example, the invention may be applicable to a biomarker or advantageously an antibody. In this instance, a linker may be utilized to link an antibody to the probe of the present invention. The linkers of the present invention may be attached with a covalent bond, a non-covalent bond and/or a neutrally charged ionic bond. The linker may also include a disulfide bond. In another embodiment, the linkers may have at least 4, at least 5, at least 6, at least 10, at least 20, at least 30, at least 40, at least 50, at least 60, at least 70, at least 80, at least 90 up to about 100 linear or straight-chain or branched carbon, nitrogen, oxygen, phosphorous, and/or sulfur atoms. In another embodiment, the linker may be an organic linker, such as, but not limited to, an amide, carbon-sulfide, ester or ether. The linker may be a small component, such as biotin or digoxigenin. In another embodiment, the linker may be a peptide, such as an epitope.

The methods of the present invention may be directed to detecting one or more stress response genes. In one embodiment, the method of the present invention may further comprise exposing an organism comprising the stress response gene to an antibiotic and determining if the stress response gene is expressed. In one embodiment, the organism may be a microbe. In another embodiment, the absence of a stress response gene indicates an antibiotic resistant organism. A stress gene encompasses genes that are increased in expression when the host cell is subjected to stress, including genes that encode for gene products that protect or defend the host cell from stress as well as genes that do not necessarily encode for stress-protective gene products per se, but that are co-expressed with other stress-protective gene products (e.g., genes that are induced for expression when stress response genes are induced for expression). Stress response genes include, but are not limited to, genes encoding heat shock proteins (e.g., AlphaB-Crystallin, AlphaA-Crystallin, GrpE, Family Hsp25, Hsp27, Hsp30, Hsp26. Cpn10/Hsp10, DnaJ, GroES, Hip, Hsp30, Hsp32, (HO-1), Hsp40, Hsp47, Hsp56, HO-2, Metallothionein, Ubiquitin, GroEL, Hsp60/Cpn60, Hsp65, TCP-1 (CCT), TCP-1 Alpha, TCP-1 Beta, TCP-1 Delta, TCP-1 Epsilon, TCP-1 Eta, TCP-1 Gamma, TCP-1 Theta, TCP-1 Zeta, DnaK, ERp72, Grp75 (mtHsp70), Grp78 (BiP), Hsc70 (Hsp73), Hsp70 (Hsp72), Hsp70B', Hsp71, Hsp110, Hsp90 Alpha, Hsp90 Beta, Grp94, Hsp83 Hsp100 Hsp100, Hsp104), oxidative stress response enzymes (e.g., Biliverdin Reductase, Cytochrome P450, Cytochrome P450 Reductase, Glutathione NEM, Heme Oxygenase-1 (Hsp32, HO-1), Heme Oxygenase-2 (HO-2), HSF1, c-Jun, iNOS, eNOS, nNOS, Superoxide Dismutase (Mn)), endoplasmic reticulum proteins (e.g., rbet1, Calnexin, Calreticulin, Erp72, Hsp47 (Colligin), Glucosidase II (alpha), Grp78 (BiP), Grp94, KDEL, Protein Disulfide Isomerase (PDI), UGGT), glucose regulated proteins (e.g., Grp58, Grp75 (mtHsp70), Grp78 (BiP), Grp94), stress activated kinase proteins (e.g., GCK, HPK-1, JKK1, c-Jun, Mek6, Mekk1, MeKK3, SAPK Alpha, SAPK Beta, SAPK Gamma, Sek1 (MKK4), TAK1, ZPK), degradation proteins, cell stress proteins, DNA repair proteins, lipid metabolism proteins, fatty acid metabolism proteins, sterol metabolism proteins, amino acid metabolism proteins, carbohydrate metabolism proteins, The methods of the present invention may be utilized to quantify single nucleic acid molecules by sequence type, for example, in human cells. The application generally pertains to searching for known sequences, such as but not limited to, counting transcripts from different genes (RNA) or counting marker gene sequences from different organisms (DNA).

The methods of the present invention may be utilized to detect pathogens, wherein the pathogen may be selected from the group consisting of inactivated pathogens, attenuated pathogens, or immunogenic sub-units (e.g. proteins, polypeptides, peptides, epitopes, haptens).

In an advantageous embodiment, the pathogen may be a human pathogen, such as, for instance: a Morbillivirus antigen, e.g., a measles virus antigen such as HA or F; a rabies glycoprotein, e.g., rabies virus glycoprotein G; an influenza antigen, e.g., influenza virus HA or N; a Herpesvirus antigen, e.g., a glycoprotein of a herpes simplex virus (HSV), a human cytomegalovirus (HCMV), Epstein-Barr; a flavivirus antigen, a JEV, Yellow Fever virus or Dengue virus antigen; a Hepatitis virus antigen, e.g., HBsAg; an immunodeficiency virus antigen, e.g., an HIV antigen such as gp120, gp160; a Hantaan virus antigen; a *C. tetani* antigen; a mumps antigen; a pneumococcal antigen, e.g., PspA; a *Borrelia* antigen, e.g., OspA, OspB, OspC of *Borrelia* associated with Lyme disease such as *Borrelia burgdorferi*, *Borrelia afzelli* and *Borrelia garinii*; a chicken pox (varicella zoster) antigen; or a *Plasmodium* antigen.

In one embodiment of the present invention, the pathogen may be an avian pathogen selected from the group of avian pathogens including, but not limited to, *Salmonella typhimurium*, *Salmonella enteritidis*, Infectious Bronchitis virus (IBV), Newcastle Disease virus (NDV), egg drop syndrome virus (EDS), or Infectious Bursal Disease virus (IBDV), avian influenza virus, and the like, and combinations thereof.

Alternately, the pathogen may be a feline pathogen such as, but not limited to, feline herpesvirus (FHV), feline calicivirus (FCV), feline leukemia virus (FeLV), feline immunodeficiency virus (FIV), rabies virus, and the like, and combinations thereof.

In another embodiment, the pathogen may be a canine pathogen including, but not limited to, rabies virus, canine herpesvirus (CHV), canine parvovirus (CPV), canine coronavirus, *Leptospira canicola*, *Leptospira icterohaemorragiae*, *Leptospira grippotyphosa*, *Borrelia burgdorferi*, *Bordetella bronchiseptica* and the like, and combinations thereof.

In yet another embodiment of the invention the pathogen may be an equine pathogen, such as equine herpesvirus (type 1 or type 4), equine influenza virus, tetanus, west nile virus, and the like or combinations thereof.

In another embodiment, the pathogen may be a bovine pathogen, such as rabies virus, bovine rotavirus, bovine parainfluenza virus type 3 (bPIV-3), bovine coronavirus, bovine viral diarrhea virus (BVDV), foot and mouth disease virus (FMDV), bovine respiratory syncytial virus (BRSV), Infectious Bovine Rhinotracheitis virus (IBR), *Escherichia coli, Pasteurella multocida, Pasteurella haemolytica* and the like and combinations thereof.

In yet another embodiment, the pathogen may be a porcine pathogen such as, but not limited to, swine influenza virus (SIV), porcine circovirus type 2 (PCV-2), porcine reproductive respiratory syndrome virus (PRRS), pseudorabies virus (PRV), porcine parvovirus (PPV), FMDV, *Mycoplasma hyopneumoniae, Erysipelothrix rhusiopathiae, Pasteurella multocida, Bordetella bronchiseptica, Escherichia coli* and the like, and combinations thereof.

In another embodiment, the pathogen may be a pathogenic organism (for example, infection by a virus, bacteria, fungus, or protozoan parasite).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Integrated Hybridization and Spectral-Domain Multiplexing for Rapid RNA Detection This Example relates to a method for rapid and sensitive nucleic acid detection, specifically RNA, in digital readouts without the use of PCR or other amplification methods. To this end Applicants developed a novel hybridization procedure, new fluorescent hybridization probes, microdevices, and prototype hardware and software. This enables the development of a practicable and affordable pathogen diagnostic, based on transcriptional profile measurement that transform the diagnosis and management of infectious diseases. In addition, the technologies developed find important applications in biotechnology more broadly, from low-cost, rapid, and highly quantitative RNA profiling, to improving hybridization protocols used in targeted sequencing and array-based studies, to novel applications of spectral encoding in single-cell studies utilizing the DNA origami-based probes.

Rapid, High-Yield Hybridization of Sub-Femtogram Quantities of Nucleic Acid Templates with Nucleic Acid-Based Optical Probes.

Applicants propose a combination of several methods to allow efficient probe-target hybridization in minutes inside a microfluidic device designed to accept concentrated crude lysates prepared from clinical samples and deliver probe-target complexes to a surface for high-speed analysis by wide-field optical microscopy. Applicants build and test devices to demonstrate the speed, sensitivity and cost enhancements gained as a result of lab-on-a-chip automation, elimination of sample loss, increased probe and target concentration, and optimized buffer and thermal conditions during hybridization. Applicants reduce the time from lysate acquisition to a ready-to image array of probe-target complexes from ~12 hours by the most closely related commercial method to less than 60 minutes.

Single-Molecule Detection of Transcripts with DNA Origami-Based Spectral Barcodes.

A DNA nanotechnology approach to optical barcoding has many advantages, including the ability to straightforwardly encode multiple brightness levels in three color channels to optically barcode hundreds of probes for different mRNA molecules in the spectral domain only (no spatial resolution is required within a given barcode). Applicants validate hybridization and co-imaging of spectral barcodes using a wide-field optical microscope. The flexibility of the specific DNA origami approach Applicants have identified facilitate advancements in biological resolution, optical readout speed, and allow simplification of instrumentation needed for readout. In combination with the ready availability of fluorescent oligonucleotides, this is an attractive approach for both early development and deployment at large scale and low cost.

Implementation and testing of simplified instrumentation for hybridization and Detection.

Applicants prototype a series of simplified, low-cost instrument components capable of executing the RNA targeting assay at high target multiplicity and high speed. The fluidic and optical designs realize the speed, sensitivity, simplification and cost dividends of advancements made in Aims one and two, as demonstrated by counting >100 transcript types with 1000-fold dynamic range within a few hours or less from sample to answer. The component design is made to interface seamlessly with sample prep components to allow integration into a single, commercial-style diagnostic instrument (total cost <$50,000). These prototype instruments, control systems, associated software, and the probe sets is made available to and supported in other component efforts for evaluation, testing, and pursuit of their respective goals.

The treatment of routine and life-threatening infectious disease would be revolutionized by a rapid test for pathogen identification and drug sensitivity. The rising incidence of resistance in increasing numbers of strains and the threat of bioterrorism place a premium on universal approaches able to detect previously uncharacterized resistance traits (Davies et al. Microbiology and Molecular Biology Reviews. 2010; 74(3):417; Robicsek et al. Nat Med. 2006; 12(1):83-8; Wongsrichanalai Trends in Parasitology. 2001; 17(7):307-9). Culture-based methods for pathogen identification and susceptibility testing are slow (>1 day), labor-intensive, and require many separate measurements to cover a large number of pathogen types and drugs. Rapid, universal identification of pathogen types and drug susceptibilities is a key driver in patient outcomes and epidemic control (Wongsrichanalai Trends in Parasitology. 2001; 17(7):307-9; Lawn et al. Int J Tuberc Lung Dis. 1997; 1(5):485-6; McIntosh Clinical Chemistry. 2003; 49(6):845-6; Rolland et al. Tropical Medicine & International Health. 2006; 11(4):398-408).

Established concepts for pathogen detection and antibiotic susceptibility in the molecular diagnostics space focus on PCR amplification of genomic loci specific to different classes of organisms or previously characterized resistance mechanisms (Boehme et al. New Engl J Med. 2010; 363 (11):1005-15). This approach is hampered by the amplification reactions required to produce a detectable signal. The need to remove PCR inhibitors from the sample prior to analysis imposes a requirement for nucleic acid purification, adding cost, complexity, and time to the diagnostic process (Al-Soud et al. Journal of Clinical Microbiology. 2001; 39(2):485-93; Yun et al. Korean Journal of Clinical Microbiology. 2011; 14(3):97-102). Finally, the production of a high concentration of amplicons creates a tremendous potential for false-positive results from product contamination (Millar et al. Journal of Clinical Microbiology. 2002; 40(5): 1575-80). Attempts to address the contamination problem in PCR invariably lead to complex instrumentation, longer assay times, and higher assay cost (Tetzner. Methods Mol Biol. 2009; 507:357-70).

By contrast, this Example develops a proven concept for pathogen identification and susceptibility by direct, amplification-free RNA profiling that has a strong potential to serve as a universal (many pathogen types, many drug types, de novo-resistance-capable) and rapid platform for pathogen identification and drug susceptibility testing (Barczak et al. Proceedings of the National Academy of Sciences. 2012; 109(16):6217-22). In the original demonstration, transcriptional profiles were assessed using the nCounter platform from NanoString (Seattle, Wash.) (Geiss et al. Nat Biotechnol. 2008; 26(3):317-25). This single-molecule hybridization-based approach has several advantages over amplification-dependent methods: 1) High multiplexing capacity that can support the identification and susceptibility profiling of many organisms at once (for a given drug). 2) No need for nucleic acid purification due to the low sensitivity of hybridization reactions to small molecules and proteins present in the sample that can inhibit enzymatic reactions required for nucleic acid amplification. 3) Low susceptibility to contamination from previous assays, as analytes are not amplified in the assay. 4) Excellent sensitivity to low (sub-femtogram) analyte quantities.

Notwithstanding these merits, the specific implementation of NanoString is not suitable for deployment as a clinical diagnostic, as the Nanostring assay 1) takes too long (~16 hours), 2) requires too many manual steps, 3) lacks sufficient sequence resolution for some diagnostic tasks, 4) is not formatted for integration into a streamlined workflow, and 5) requires instrumentation and reagents that are too expensive. Applicants also considered RNA-sequencing as an alternate RNA profiling methodology, discarding this approach as too slow in practice and susceptible to the drawbacks associated with amplification.

This invention is significant because it develops the rapid hybridization procedure, new fluorescent hybridization probes, microdevices, and prototype hardware and software needed to realize a practicable and affordable pathogen diagnostic based on transcriptional profile measurement, technology and hardware that does not exist today. Aside from this motivating goal, the technologies developed find important applications in biotechnology more broadly, from low-cost/rapid/amplification-free RNA profiling in eukaryotic and bacterial cells, to improving hybridization protocols used in targeted sequencing and array-based studies, to novel applications of spectral encoding in single-molecule and single-cell studies utilizing the DNA origami-based probes.

This invention relates to a hybridization-based single RNA molecule counting method that retains the advantages of the Nanostring method, but addresses the limitations in speed, cost, and resolution, while interfacing seamlessly with technologies to enable the rapid processing of urine and blood. To do so, principle advancements need to be realized: 1) the cost of fluorescent hybridization probes needs to be reduced, 2) probe hybridization needs to be driven faster under conditions that require fully-specific probe-sequence interaction, 3) a multiplexing scheme that does not require probe stretching to simplify the instrumentation and allow higher target density on the surface, 4) low-volume input capability to accept concentrated lysates. Applicants demonstrate that these objectives can be met by the application of DNA-origami based multi-level fluorescent hybridization probes combined with the samples in a microfluidic format.

Probe hybridization is the slowest step in the NanoString nCounter protocol (12 hours), and the assay results are compromised if a shorter hybridization time is attempted. Fundamentally, there is no limit on the rate of probe hybridization, which can be improved through a chemical kinetics approach by simply increasing target and probe concentrations and improving hybridization reaction efficiency. This Example describes Applicants' approach to accelerating probe-target hybridization reactions within the constraints imposed by lysate formatting, probe cost, and hybridization specificity requirements by increasing probe and target concentrations in nanoliter volumes on a custom microdevice.

FIG. 2 depicts similarities and differences between the nanostring assay and the DNA-origami based assay, which takes advantage of distinguishable fluorescence intensities across three color channels, obviating the need to resolve the sequence of the probe signals and allowing a higher surface density of probe-target complexes, facilitating faster scan speeds.

This invention is innovative because it translates biophysical chemistry concepts, custom microfluidics, DNA nanotechnology, and single-molecule fluorescence imaging to nucleic acid detection in new ways to surpass the limitations of the best current technology to meet key performance objectives necessary to the development of a practical next-generation prototype diagnostic instrument based on a powerful new diagnostics concept, pathogen RNA profiling.

Rapid, High-Yield Hybridization of Sub-Femtogram Quantities of Nucleic Acid Templates with Nucleic Acid-Based Optical Probes.

Nucleic acid hybridization exhibits extremely high sequence-specificity under the right conditions due to the highly cooperative nature of hybridization reactions (Pohl et al. Journal of molecular biology. 1972; 67(3):375-96). Mismatched base pairs can disrupt this cooperativity in RNA-DNA hybridization, making the likelihood of nonspecific hybridization interactions low under conditions that strongly favor fully matched hybridization interactions (Sugimoto et al. Biochemistry. 2000; 39(37):11270-81). Hybridization reactions are well-understood from chemical kinetics standpoint, and suited to systematic engineering approaches (Wang et al. Biochemistry. 1995; 34(30):9774-84). Another attractive property of DNA hybridization is that it is generally insensitive to interference from small molecules and proteins in solution.

Bimolecular association rates are the product of two factors: a collision rate between the interacting partners (Smoluchowski et al. Zeitschrift fur Physik. 1916; 17:557-85), and a per-collision binding efficiency (Schlosshauer et al. The Journal of Physical Chemistry B. 2002; 106(46): 12079-83). The collision rate is a function of the concentration of the molecules and an inverse function of the size of the molecules. For the highest collision rate, one desires small, fast-diffusing partners at high concentration, and the hybridization rates ($\sim 10^6$/M/s) expected for diffusion-limited association of an oligonucleotide with a larger RNA molecule have been documented experimentally (Wang et al. Biochemistry. 1995; 34(30):9774-84; Schwille et al.

Biochemistry. 1996; 35(31):10182-93), proving that there is no fundamental impediment to rapid association of DNA probes with RNA.

Accelerating Hybridization Kinetics

Applicants propose a combination of several methods to allow efficient probe-target hybridization within minutes. Hybridization reactions are slowed by entropic barriers for nucleation that are large at high temperature and sequence-dependent enthalpic barriers at low temperature (Yin et al. Accounts of Chemical Research. 2011; 44(11):1172-81). The sequence-dependent enthalpic barriers arise from internal structure of the targets and probes, leading to a distribution of optimum hybridization temperatures in any multiplexed hybridization assay.

Maximizing Target and Probe Concentrations for Rapid Hybridization

One of the lowest-yield steps in many nucleic acid preparation procedures is nucleic acid purification. Applicants avoid the delay and sample loss associated with purification since Applicants' assay runs in crude lysate.

Several measures are taken to maximize the RNA target concentration in the hybridization reaction. Pre-assay target loss is minimized by inhibiting hydrolysis of the RNA and adsorption to surfaces, while dilution of the RNA is carefully limited. An integrated microfluidic system (microbore capillary delivery and subsequently on-die integration) is designed to accept 50 nL of concentrated lysate. The lysate is treated with proteinase K in a buffer tuned to maximize proteinase K activity while minimizing RNAse activity (50 mM Hepes pH 7.0, 100 mM NaCl, 100 mM EDTA, 0.5% SDS), preventing adsorption of nucleic acids to surfaces and promoting probe hybridization (Schlapak et al. Langmuir. 2006; 22(1):277-85; Schlapak et al. Langmuir. 2007; 23(20): 10244-53). Streptavidin, used to recruit target RNA molecules to the surface for imaging by the capture probe, retains the ability to bind biotin after proteinase k digestion (Ellison et al. Protein Science. 1995; 4(7):1337-45), and non-digestible mutants are known (Hytonen et al. Journal of Biological Chemistry. 2005; 280(11):10228-33).

Figure 3A:
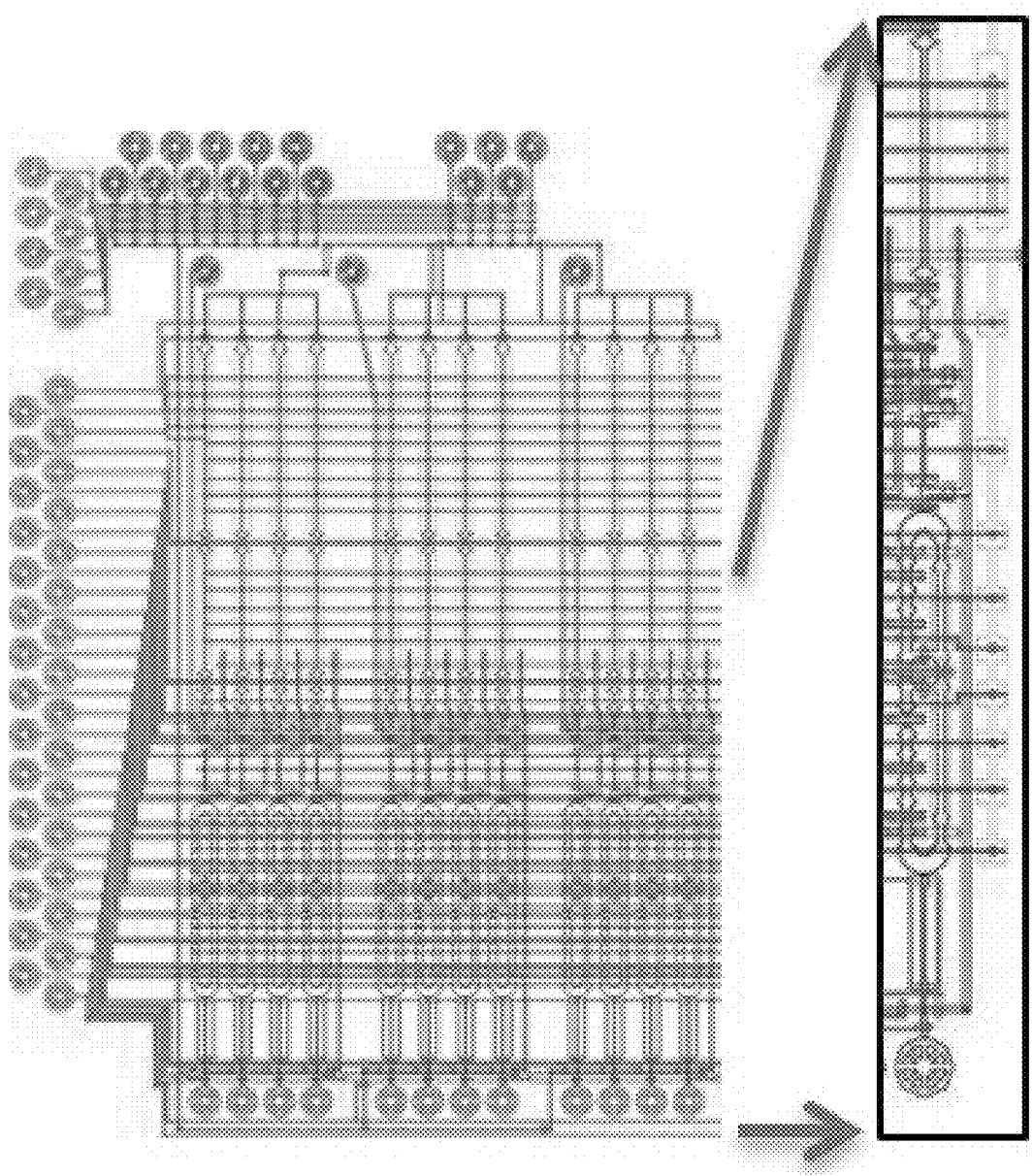
FIG. 3A-3C depicts a microfluidic reactor chip design and control/single-molecule imaging system. A) Design for reactor device similar to that needed for the proposed RNA profiling assay. Inset: the metering/mixing ring is shown in blue, the imaging area in green on the right; red channels form the control layer that operates microfabricated valves and pumps that control flow. B) Chip of the design shown in part A mounted on a number one coverslip for high-performance optical microscopy and filled with dye to visualize the channel structure. C) Photograph of a chip mounted on a Nikon TI-E microscope setup in the Blainey Lab fitted for chip control and single-molecule detection. The stage insert is a custom design printed on a 3D printer at the Broad Institute, and is an example of our ability to effectively prototype high-quality, deployable instrument components.
Figure 3B:
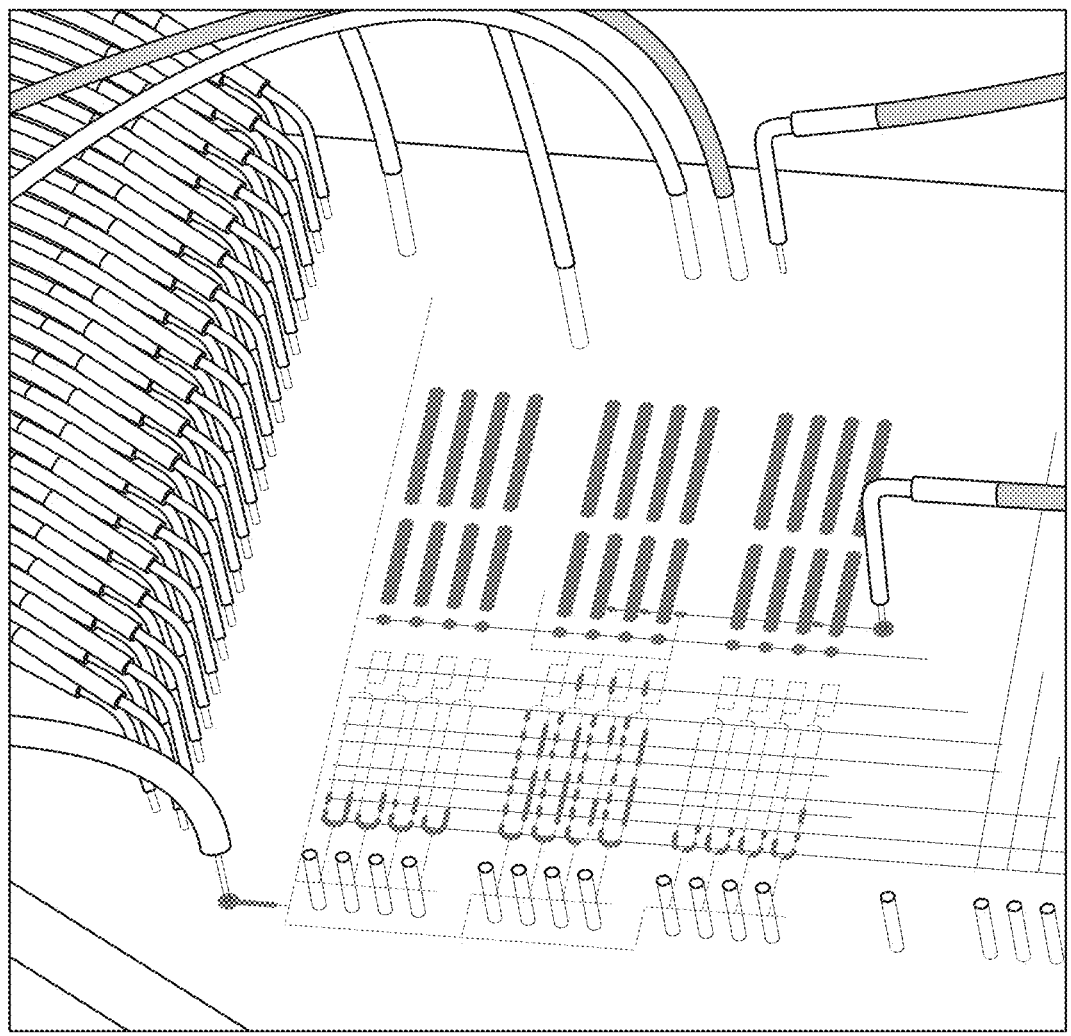
Figure 3C:
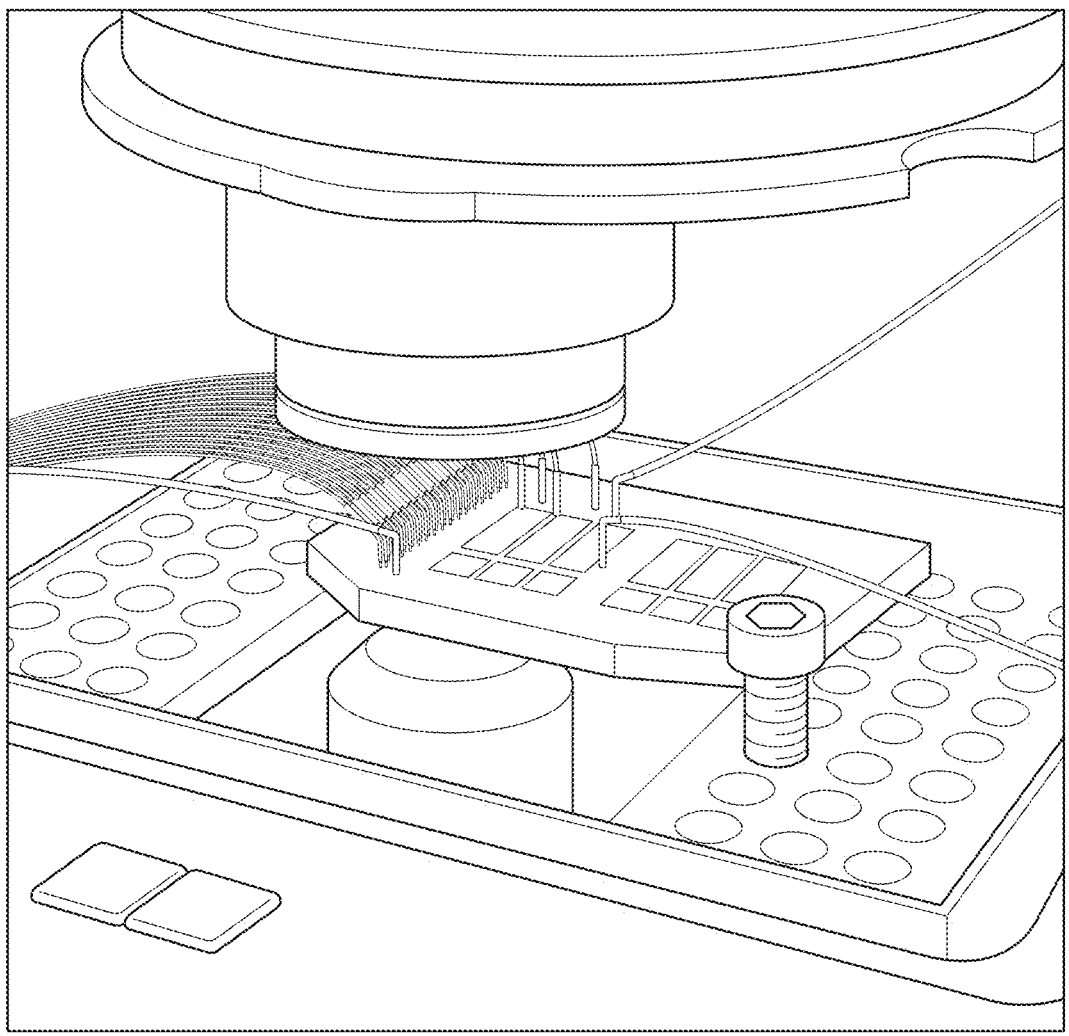

The low hybridization reaction volume <200 nL allows the economical application of high probe concentrations to drive the probe-target binding rate several thousand-fold higher than possible in the Nanostring assay (see FIG. 2). For example, applying 100 multiplexed probes at a concentration of 1 micromolar each requires a total of only 1 picomole of probe in a 100 nL reaction. The concentrated RNA targets and probes are actively mixed in a ring-shaped microfluidic mixer (Hansen et al. P Natl Acad Sci USA. 2004; 101(40):14431-6) similar to that which Applicants have already created (see FIG. 3).

To reduce the incidence of self- and cross-hybridization, as well as to increase the biological resolution of the assay, the hybridization probes are designed to bind complementary regions of the target RNA molecules 14-26 bases in length with a target melting temperature of 55 C. This differs from typical Nanostring probes, which are designed with ~50 base pairs of target complementarity and are applied under conditions that require only ~85% complementarity with the target for binding (Geiss et al. Nat Biotechnol. 2008; 26(3):317-25). The loose requirement for complementarity of the Nanostring probes is a significant impediment to discrimination of closely related species/strains of pathogens. In response to design constraints, Applicants tune the hybridization conditions to require perfect complementarity or allow a single mismatch.

Maximizing Binding Efficiency and Assay Specificity

Hybridization of proximal probe and target molecules is impeded by entropic free energy barriers at high temperatures (Yin et al. Accounts of Chemical Research. 2011; 44(11):1172-81). At lower temperatures, sequence-dependent enthalpic free energy barriers exist when the probe and/or target contain internal or cross-hybridization structure. Applicants plan to efficiently capture all the hybridization interactions by thermally annealing from 55 C to destabilize undesired probe and target structures and favor rapid formation of the desired specific probe-target hybridized structures. By so doing, Applicants capture the desired hybridization products while accelerating the formation of yet-unformed interactions by ramping the temperature down to 25 C over the course of 30 minutes (subsequent testing evaluates the speed-yield tradeoff). Thermal annealing is commonly used to achieve rapid and specific annealing of oligonucleotides to single-stranded targets (eg in transition from the melting step to the priming step in PCR), but not in the Nanostring procedure. Applicants' assay, like Nanostring, requires hybridization of both the fluorescent spectral probe and the capture probe to produce a signal, so the probability of producing a false-positive signal is very low.

Assay Workflow

FIG. 2 shows the workflow steps and device for the new assay that enables fast, high-yield hybridization. The device is placed on a flat-top thermocycler for easy testing of different temperature profiles while the sample and probes are mixed in the ring-shaped structure. Subsequent to hybridization, valve states are reconfigured and buffer added to allow the mixture to be pumped through an imaging region where the biotinylated capture probes (both free and in complex with targets and reporter probes) bind the streptavidin-coated bottom surface of the imaging region. Here the microfabricated approach lends both speed and sensitivity advantages over Nanostring. The 100-fold higher concentration of probe-target complexes in the assay increases the surface-binding rate by the same factor, with the dividend freely chosen to apportion across the speed-yield tradeoff. Secondly, because the entire volume of the hybridization reaction is introduced to the imaging region, a significant sensitivity advantage (30-fold) is gained vis a vis Nanostring, where the imaging region holds only $\frac{1}{30}^{th}$ of the prepared sample and no active cycling of the solution is applied.

After surface capture, the imaging area is flushed with a controlled flow of buffer to remove excess probes, non-target RNA and other components. This flow is applied for a controlled time at a calibrated temperature to allow kinetically unstable non-specific complexes to be disrupted and flushed away (the difference in equilibrium constant is known to be the result of higher off-rates for mismatched DNA/RNA complexes (Wang et al. Biochemistry. 1995; 34(30):9774-84). The remaining, stable probe-target complexes are then ready for imaging with low fluorescence background. During development, this is carried out on a commercial inverted fluorescence microscope equipped with an LED epifluorescence illuminator and scientific-grade detector. Separately, custom optical microscopes are prototyped and tested in the context of a commercial-style diagnostic instrument. These microscopes can less expensive than commercial research microscopes because they are built for a single purpose and can be constructed from commodity componentry.

Assessment of Hybridization Performance

Applicants estimate the diffusion-limited pseudo-first order reaction kinetics of target binding (1 micromolar probe concentration) at $10^5/M/s \times 10^{-6} M = 0.1/s$. Given 0.2 fg of a single target transcript (~300 target molecules) in a 100 nL reaction (~5 femtomolar target concentration), Applicants expect the majority of the target molecules to be bound in less than 10 seconds at an optimal reaction temperature that minimizes free energy barriers. In principle, this allows very fast annealing rates, although Applicants outline a conservative 30 minute ramp (approximately one degree per minute) as a starting point.

Applicants' performance target is 80% hybridization yield (spectral probe+RNA+capture probe bound to surface in the imaging area) for 0.2 fg of a given target transcript (about 300 1000 bp RNA molecules) in less than 1 hour. This target is conservative given that the ultimate limit based on diffusion rates is in the range of seconds for probe-target assembly in solution (FIG. 2), and surface-binding times estimated in the range of minutes (calculations not shown). To assess and improve hybridization performance (rate and yield), probe-target complex density in the imaging region is measured as functions of probe concentration, annealing rate/time, buffer composition, and surface capture time. Initially, the template is purified total RNA from (*E. coli* RB1 clinical isolate) and transcripts from three genes (recA, uvrA, and dinD) is targeted by simple hybridization probes labeled three color channels adapted from those previously reported (Barczak et al. Proceedings of the National Academy of Sciences. 2012; 109(16):6217-22). By targeting two singly-labeled probes per RNA transcript and assessing the distribution of probe labels per target by photobleaching analysis as a function of hybridization reaction time, Applicants can assess hybridization efficiency independently of probe labeling efficiency. Next, the same rate/yield analysis is carried out on concentrated crude lysates of the same organism with 10, 1000, 100,000 bacteria in 50 nL lysate volumes (100 nL hybridization reaction volumes) to determine the concentration-dependent effects of cellular components on the hybridization reaction.

Applicants are prepared to handle several contingencies that may arise. If RNA is degraded in the chip, Applicants increase the stringency of protease treatment of the lysate, include an RNAse inhibitor cocktail, and treat the device to destroy any RNAse by UV irradiation or hypochlorite wash prior to substrate bonding. RNAse activity can be detected by lysis hold time-dependent target count suppression using a calibrated input and confirmed by degradation of a run-off transcript of known length to lower molecular weight incubated in the device with lysate and recovered for analysis in a mock RNA quantification experiment.

If solution hybridization does not meet Applicants' goal metric based on the above approaches, additional measures are taken. The effective concentration of nucleic acids is increased by adding low molecular weight glycols to crowd the solution (Amasino et al. Analytical Biochemistry. 1986; 152(2):304-7). The electrostatic repulsion between binding partners is reduced by increasing ionic strength (monovalent ions), by linking the probe to a positively charged element, or eliminated by introducing a peptide nucleic acid (PNA) probe chemistry, previously shown to dramatically accelerate hybridization rates (Nielsen et al. Curr Issues Mol Biol. 1999; 1(1-2):89-104). If a significant entropic barrier to hybridization is suspected (slow hybridization of structure-free probes at higher temperatures), a locked nucleic acid (LNA) base is incorporated in the probe to allow a shorter probe and pre-organize the probe for hybridization (both effects reducing the entropic nucleation barrier) (Vester et al. Biochemistry. 2004; 43(42):13233-41). If enthalpic barriers are suspected (slow hybridization of probes with internal structure at lower temperatures), the initial temperature and/or annealing ramp is increased, additives that stabilize single-stranded nucleic acids relative to double-stranded nucleic acids such as DMSO or *E. coli* single-stranded binding protein is employed, and more stringent efforts to avoid probe and target internal structure and cross-reactivity is taken (Chakrabarti et al. Gene. 2001; 274(1):293-8).

If surface capture is found to be slow in surface-capture-time dependent experiments, or the capture probe concentration required for fast kinetics results in too many unreacted capture probes that swamp binding sites in imaging area, the following additional measures are taken. The unreacted capture probes are depleted by dilution or separation on beads or a surface segment functionalized to bind free probe on a selective basis (alternatively, the capture probes can be pre-loaded on the imaging area surface, and target RNA captured to the surface by a hybridization interaction rather than a biotin-streptavidin interaction). The geometry of the imaging region is altered to increase the ratio of active surface area to volume. Finally, the surface density of streptavidin for binding the biotinylated capture probe is enhanced by loading the streptavidin monolayer with a multiply-biotinylated polymer or structure (DNA-based or synthetic) to which additional streptavidin tetramers can be bound, increasing the number of capture sites and enhancing their display.

Single-Molecule Detection of Transcripts with DNA Origami-Based Spectral Barcodes.

The requirement of multiplexing across of hundreds of targets at once places strong constraints on the probe design in the new RNA-profiling assay. To meet Applicants' goals of very high probe density on the surface of the imaging region and the ability to image a large region at once, Applicants require a multiplexing scheme with high signal intensity and encoding only in the spectral domain (no spatial component as per NanoString). To do so, the number of colors can be increased, eg by expanding the spectral range and utilizing emitters with narrower emission spectra such as quantum dots, encoding spatial relationships in the spectral channel, or by utilizing multiple distinguishable intensity levels in a small number of color channels. The latter approach is selected for this application as the most feasible to meet goals.

Multi-Level Spectral Coding

By encoding n absolute intensity levels in each of m spectral channels, an $n^m$-plex encoding capability is created. For example, if n=six intensity levels are encoded in m=three color channels, $6^3$=6×6×6=216-plex capacity is generated. Such schemes have been commercialized for polymer beads [Luminex reference], but Applicants are not aware of an application of multi-level encoding at any significant multiplex scale at the single-molecule level (Li et al. Nature biotechnology. 2005; 23(7):885-9). This leaves open the question of how to create multi-level probes for Applicants' assay. Applicants favor a structure structure, wherein the number of fluorophores can be encoded deterministically when the structure is being built generation-by-generation by the inclusion of unlabeled monomers or monomers labeled with organic labels in each generation. The deterministic placement of dyes in the structure is key to generating multiple, sharply-defined intensity levels in a small structure containing less than 100 labels in total. Such a structure could be constructed by chemical synthesis using one of many synthetic organic structure chemistries that have been demonstrated, or alternatively, using DNA origami technology (Li et al. Nature materials. 2003; 3(1):38-42; Rothemund. Nature. 2006; 440(7082):297-302). The structure approach has two unique advantages. First, structures can be constructed step-wise from a simple set of starting materials. Second, the structure approach is flexible, with the number of encoded intensity levels, intensity of the lowest intensity level, and the spacing between intensity levels chosen with great freedom by varying the number of generations in the structure and the placement of labeled monomers within it.

DNA Structure-Based Spectral Probes

Applicants prefer a nanostructured DNA structure approach because DNA structures are 'natively addressable' to nucleic acid targets, can be produced cheaply in high yield and high purity by taking advantage of programmed hybridization interactions stabilized by covalent ligation, and dye conjugation can be outsourced to high-quality commercial oligo vendors.

Specifically, Applicants favor the construction of DNA structures based on three-way DNA junctions such as those previously reported (Li et al. Nature materials. 2003; 3(1): 38-42), where up to $5^{th}$ generation structures were assembled in high yield without purification. A branched DNA origami structure is better for constructing the needed probes than a linear structure assembled from overlapping oligonucleotides because in the structure, a large number of intensity levels can be encoded in a small number of steps (n coupling steps produces $[2^{(n+1)}-1]$ nonzero intensity levels in Applicants' scheme, or $1+3(2^n-1)$ for a three-branch scheme), whereas in a linear structure built step by step, the number of intensity levels created scales only linearly the number of coupling steps.

The smaller number of coupling steps required to produce structure probes with a given number of encoded levels is critical to the production of a large number of differently encoded probes each in high yield without onerous purification steps. Another advantage of the three-way junction scheme is that up to three dyes per tile can be included using singly-labeled oligonucleotides, since a tile is composed of three oligonucleotides. This approach could be used to make the intensity levels easier to distinguish by increasing the size of the intensity difference between levels (eg a spacing of three label units per level). Alternatively or in addition, the spacing between levels can be doubled by creating a structure with one additional generation and deploying tiles in pairs for the purpose of encoding. In any scheme, the lowest few intensity levels can be intentionally left dark to increase the minimum intensity that needs to be detected. This is important both for allowing detection in larger fields of view by simpler, smaller, and less expensive optical systems, and also to accommodate spectral crosstalk in certain implementations.

Synthesis of DNA Structure Spectral Probes

Figures 4A, 4B:
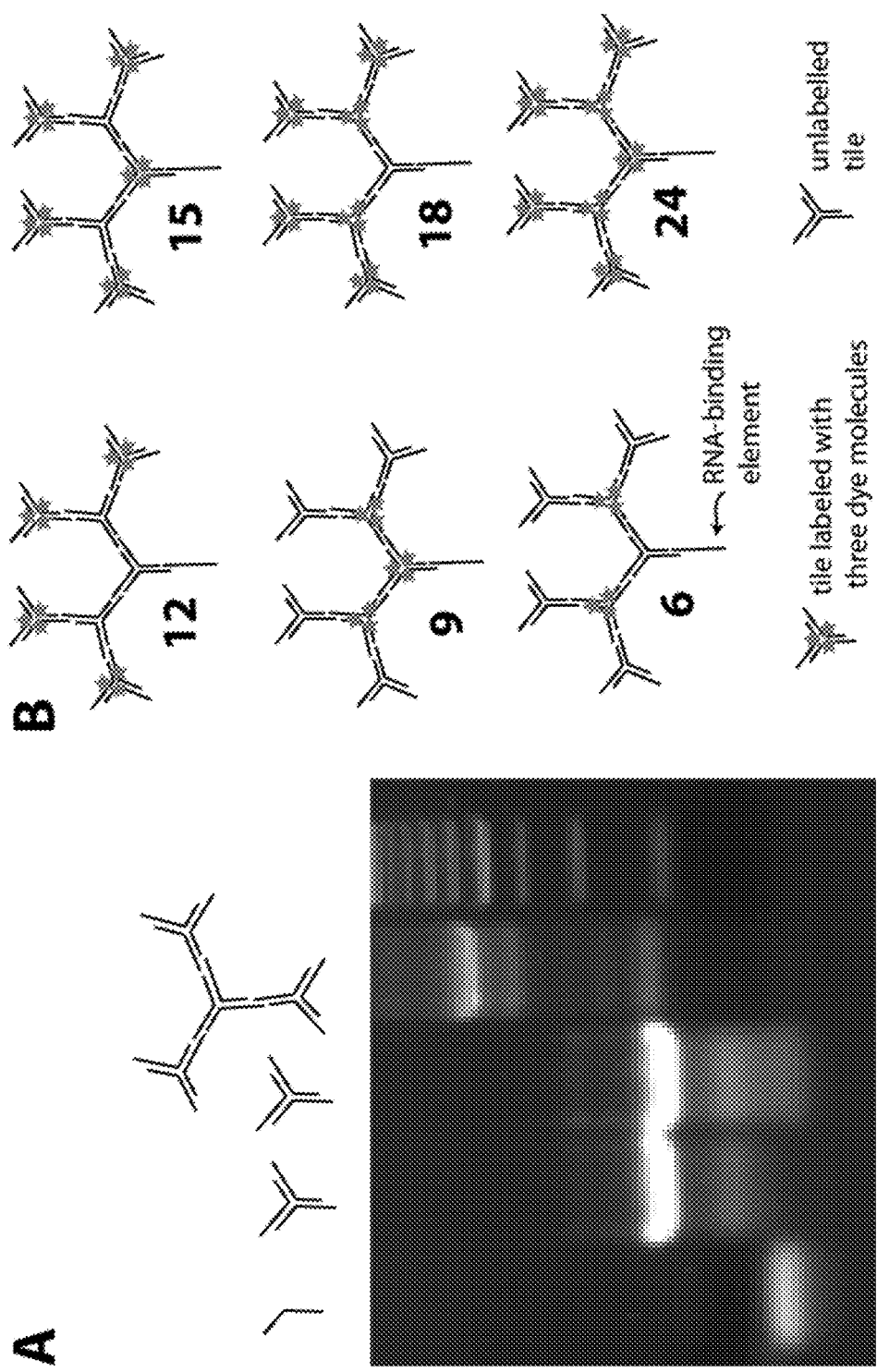
FIG. 4A-4B depicts a DNA structure assembly from three-way junction 'tiles'. A) gel image of structure assembly process. Lane 1, oligo component; 2, tile type A; 3, tile type B; 4, first generation structure composed of tile types A and B, 5, 50 bp DNA ladder. See contingency 2.3.2.6 for details on purity. B) Schematic showing six intensity levels in a second-generation structure, with number of dye molecules per structure indicated (increments of three dye molecules starting from six).

Applicants assemble third-generation DNA structures from three-way junction tiles where one arm of the seed tile is appended with a single-stranded DNA oligonucleotide designed to hybridize to the target RNA. Such structures consist of a total of seven tiles assembled in two sequential annealing/ligation steps that Applicants expect to produce the desired structures in high yield without purification based on the literature (Li et al. Nature materials. 2003; 3(1):38-42) and FIG. 4. This 'second-generation' structure allow the encoding of up to seven equally-spaced intensity levels, where the intensity interval is three labels per level (located near the three-way junction to avoid interference with the annealing and ligation reactions). Assigning multiple labels per level makes the levels more distinguishable not only by increasing brightness, but also by averaging over stochastic photophysical dynamics of the labels.

Imaging Single DNA Structure Spectral Probes

RNA targets are enumerated by counting target-probe complexes recruited to the surface of the device imaging area. Applicants have already demonstrated molecular recognition and counting by wide-field fluorescence microscopy in simplex (see FIG. 5). In principle, Applicants can create very high theoretical multiplexing capacities (eg $46^4=4,477,456$ combinations in a fifth-generation three-branch scheme in four colors), the useful number of levels per color is practically limited by the spectral cross-talk of the optical detection system. Specifically, the light bleeding from the highest encoded out-of-channel intensity must be less than the lowest encoded within-channel intensity. Thus, the ability to drop out the lowest few channels relaxes the requirement for optical contrast ratio across the spectral channels. Even without dropping channels, the high-quality optical filters available today and judicious choices of fluorescence excitation and detection bands allow more than 20 intensity levels per color channel to be resolved. In fact, the practical limit on the number of distinguishable levels is likely to be driven by mundane considerations such as the illumination intensity across the imaged area (see FIG. 5). The extreme flexibility of the DNA origami structure approach and the commercial availability of high-quality building blocks makes this approach likely to succeed.

Assessment of Spectral Barcode Imaging Performance

A set of structures encoding seven intensity levels with Cy3 is synthesized and tested in targeting a biotinylated single-stranded DNA target both in solution and when the target is presented on a surface. Applicants assess the ability to resolve the different intensity levels by imaging engineered mixtures of structures encoding different combinations of intensity levels and comparing Applicants' calls with the known composition of the mixture. The increase of fluorescence intensity with increasing numbers of labeled tiles is calibrated in these experiments. Note that a linear increase in fluorescence with the number of labels in a structure is not a requirement for this assay, in fact sub-linearity may constitute an advantage by compressing the dynamic range required of the detector. Applicants also evaluate the possibility of getting additional information about the number of labels per target by counting steps in a photobleaching trajectory from each probe-target complex (Zhang et al. RNA. 2007; 13(10):1793-802; Engel et al. The Journal of cell biology. 2009; 187(1):81-9).

Next, Applicants synthesize two additional sets of seven differently-labeled structures, with Cy5 and Fluorescein respectively, to complete a library of 21 structures (seven intensity levels in three colors). Combinations of structures from this library yield $7^3=343$-plex multiplexing capacity with signal in each bin. To demonstrate this capability, one structure of each color is targeted to synthetic DNA scaffolds targeted in turn to a biotinylated single-stranded DNA target and the most challenging color/intensity combinations tested as described above. To validate the performance of the probes on mRNA, the same experimental progression is employed (purified RNA, crude lysate from lab cultures, crude lysate from clinical samples, with the exception that the assay is tested in a minimum 100-plex format with probes targeting at least five different pathogenic organisms. These assays include nonspecific probes for which no targets exist (negative controls to assess nonspecific binding) as well as positive-control probes targeting biotinylated DNA targets spiked into the lysate at known concentrations. Scripts automating the acquisition of images, and signal identification/counting from many fields of view be developed in the course of this testing.

If ligation of the tiles is insufficiently complete, Applicants extend the stem region of the tiles to space the ligation sites farther from the three-way junctions (where the fluorophores are located as 'internal' modifications), and increase the amount of ligase used. Alternatively, Applicants make the tile-tile interactions thermally stable independent of ligation by designing long, GC-rich overlaps to link the tiles.

If the optimized yield of properly assembled second-generation structures is not sufficiently high for direct application, Applicants purify the probes in solution on a functional basis, in a manner conceptually similar to that used by Nanostring to purify their probes (Geiss et al. Nat Biotechnol. 2008; 26(3):317-25). Hybridization motifs can be engineered into tiles such that only properly assembled structures display the complete set of single-stranded motifs. Then, by selective and/or subtractive steps entailing the hybridization of probes to complementary oligonucleotides borne by magnetic beads, Applicants can purify properly assembled probes. Such a strategy can be applied to the final pool of oligos, such that a single purification step can purify an entire probe library.

If the structures are too sticky for surfaces in the device, Applicants attach DNA hairpins to stabilize the unoccupied tile sites and reduce the number of unpaired bases in the structure. Applicants also tune the ionic and surfactant content of the buffers to prevent nonspecific interaction of the probes with surfaces. Note that the poly(ethylene glycol) graft surfaces Applicants use on the bottom substrate are known to be extremely effective in suppressing the adsorption of both proteins and nucleic acids. Protocols are also available to graft PEG onto PDMS surfaces if Applicants deem the coating of all interior surfaces of Applicants' devices to be necessary (Wong et al. Microfluid Nanofluid. 2009; 7(3):291-306).

If the different intensity levels are too difficult to distinguish, Applicants design a larger interval (as large as the emission of eight labels) between each fluorescence intensity level and incorporate photobleaching step analysis. If spectral crosstalk is too high Applicants reduce crosstalk by narrowing and shifting the excitation and emission bandpass regions, drop the lowest intensity level from the encoding scheme, and/incorporate photobleaching step analysis.

If the probes are found to be insufficiently specific under Applicants' hybridization conditions, Applicants increase the final temperature of the hybridization reaction to disfavor formation of nonspecific complexes and make the wash step after binding in the imaging region more stringent (duration, temperature, and lower ionic strength) to a calibrated degree based on analysis of the retention of control probe-target complexes of known thermodynamic and kinetic stabilities. Additionally Applicants can locate the termini of the signal and capture probes, such that they can be ligated after surface capture and a mild wash. Nonspecific probes on a target are not likely to be adjacent and ligated, such that they could be removed selectively in a subsequent stringent wash.

Implementation and Testing of Simplified Instrumentation for Hybridization and Detection.

To make an impact on the public in the diagnostics space, the innovations described herein are translated into a practical (easy-to-use, reliable, low-cost) instrument appropriate for placement in a clinical diagnostics lab at a hospital or community clinic.

General Approach to Prototype Development

In order to reduce the new RNA detection method to clinical practice, this translates the hybridization and imaging steps to a miniaturized platform constructed from commodity mechanical, electronic, and optical components. Applicants design and build such hardware and software to accept nanoliter-scale samples of concentrated lysate and control the hybridization and imaging steps. The diagnostic instrument take the form of a desktop device the size and weight of a household microwave. The chip element has an inexpensive consumable encompassing the concentration, drug exposure, and hybridization elements pre-loaded with antibiotics and probes. Inside the box is a microfluidics control module, a thermal control module, and the optical system for fluorescence readout.

Probe-Target Hybridization Subsystem

The Hybridization Module is Naturally compact and scalable to a large number of samples as a result of the microfluidic miniaturization and integration. The existing reactor/imaging chip is already set up to process 24 samples, and is scaled down to process a single patient sample divided eleven ways (exposure to ten drugs plus identification) and integrated at the die level with the upstream prep components.

Optical Subsystem

With respect to the optical subsystem, Applicants design and build a compact fluorescence microscope purpose-built for automated, high-speed imaging of target-probe complexes in the imaging areas of the microfluidic devices. The hybridization chip is mounted on a commercially available heating platform for temperature-controlled hybridization and wash steps, then moved in a single linear motion onto a three-dimensionally-printed receptacle similar to that shown in FIG. 3 that serves as a microscope stage. This transfer step allows better utilization of the instrument as a second sample can undergo hybridization while the first is being imaged.

Above the stage is a light emitting diode array with filtered LEDs in three colors, each tuned to excite one of the three colors in the optical barcode. Beneath the stage is located a 20× or 40× air objective on a focusing mount. Large field-of-view and high target surface density allow imaging of many probe-target complexes in just a few fields of view. A two-axis programmable translator with a spatial precision of 50 micron or better allow automatic scanning of the imaging area on the microdevice by moving the chip holder with respect to the fixed objective lens. A motorized filter wheel in the emission path include four positions, one to filter the emission of each color in the optical barcodes, plus a blank position for focus registration on fiducial marks in the sample (microfabricated features or beads randomly scattered in the imaging area) under low-intensity illumination. The light collected by the objective lens is focused on a high-resolution, low noise, low speed, charge-coupled device (CCD) array image sensor. Unless photobleaching step analysis is specified, a single long integration image in each color channel is recorded from each field of view onto the laptop or tablet computer controlling the instrument.

Software Development and User Interface

Software, written in Matlab and compiled as a stand-alone executable (requiring no software license), control the fluidics module, stage, focus mount, filter wheel, LED light source, and camera. Probe counts are made by image analysis routines, essentially identifying probe-target complexes by image thresholding and integration of photon counts above background in a neighborhood. The intensity level for each color channel for each target is determined using a previously defined calibration for the probe configuration/buffer condition used, and diagnostic calls made for each sample at the conclusion of the run. These control systems and analysis algorithms sit behind a simple user interface that steps the user through sample and microdevice loading while verifying these steps have taken place by reading microswitch states.

Standard Operating Procedures and Performance Validation

Test samples and standard operating procedures are established for this instrument. A test device with a defined concentration of the three labels employed in the assay spin-coated on the surface is used to verify that the excitation uniformity and the optical crosstalk are within specification across the field of view. A 'test analyte' mixture of synthetic RNA sequences (produced by in vitro synthesis of run-off transcripts) is used to validate overall instrument performance.

Instrument Placement

Applicants build a series of hybridization and imaging systems for deployment within other components and at field sites. The first deployed instrument is a breadboard development system built around a commercial microscope. Subsequently, three compact (commercial instrument-style) hybridization and imaging systems are constructed for deployment and testing within the biological and clinical components.

If sufficiently uniform illumination is difficult to achieve by engineering the LED projection scheme geometry and by adding light-diffusing elements, Applicants alternatively project the light in a Köhler illumination geometry from a white LED with an additional optical filter wheel on the illumination side, or simply calibrate the instrument to correct for systematic variation in illumination intensity recorded using the test sample.

If the images are too noisy with lower-power objective lenses, there are a number of measures Applicants can take. First, Applicants could move to an immersion objective with higher numerical aperture to improve the light-gathering power of Applicants' system. This is feasible since Applicants have formatted the hybridization microdevice on a number 1 glass coverslip, allowing use of close working distance objective lenses. For example, 20× objective lenses with numerical apertures up to 0.75 are readily available, and the advantage in field of view (hence scan speed) over higher-power 60× or 100× objectives is considerable (9-fold and 25-fold, respectively). Thanks to the adaptability of Applicants' DNA origami based probe design, Applicants also have the ability to increase minimum signal intensity and level spacing by altering the probe configuration.

Example 2

$G_1$ Synthesis.

Individual three way junction DNA tiles ("Ys") were formed by mixing 10 uL of each of the three necessary oligos (initial concentration of 100 uM) and then adding 70 uL of TE buffer (+0.01% Tween 20, +100 mM NaCl, +10 mM MgCl2) for a final concentration of 10 uM for each of the three individual oligos (10× dilution). The mixture was thermocycled per the program outlined in Table 3 of "Dendrimer-like DNA-based fluorescence nanobarcodes" (Soong Ho Um et al., Nature Protocols, 2006). For the two member $G_1$, 5 uL of T4 DNA Ligase (400,000 U/mL, New England Biolabs), 10 uL 10× buffer for T4 DNA Ligase with 10 mM ATP (New England Biolabs), 20 uL Y0, 20 uL Y1a, and 45 uL of milli-Q were mixed and left at room temperature for 16 hours for complete ligation. For the three member $G_1$, 5 uL of T4 DNA Ligase, 10 uL 10× buffer for T4 DNA Ligase with 10 mM ATP, 13 uL of Y0, 13 uL of Y1a, 13 uL of Y1b, and 45 uL of milli-Q were mixed and left at room temperature for 16 hours for complete ligation. All ends designed to participate in ligation had 4 bp 5' phosphorylated overhang adapters.

One-Step $G_2$ Synthesis.

Adapters were selected to prevent nonspecific ligations. Individual Ys were formed by mixing 10 uL of each of the three necessary oligos (initial concentration of 100 uM) and then adding 70 uL of TE buffer (+0.01% Tween 20, +100 mM NaCl, +10 mM MgCl2) for a final concentration of 10 uM for each of the three individual oligos (10× dilution). The mixture was thermocycled per the program outlined in table 3 of "Dendrimer-like DNA-based fluorescence nanobarcodes" (Soong Ho Urn et al., Nature Protocols, 2006). Once Y structures were formed, 5 uL of T4 DNA ligase, 10 uL of 10× buffer for T4 DNA Ligase with 10 mM ATP, 22.9 uL of Y2, 5.7 uL of Y1a, 5.7 uL of Y1b, 5.7 uL of Y0, and 45 uL of milli-Q were mixed and left at room temperature for 16 hours for complete ligation. The $G_2$ was synthesized with 4 unique Y structures. $Y_{1a}$ and $Y_{1b}$ were designed to both have adapters complementary to the $Y_2$ ligation adapters. $G_1$ formation was made possible by having 4 bp, 5' phosphorylated overhang adapters, while $G_2$ formation was made possible by having 8 bp, 5' phosphorylated overhang adapters.

$Y_{1a}$ and $Y_{1b}$ are different $Y_1$ tiles (tiles within the set of tiles $Y_1$), which can each be ligated to $Y_0$ and $Y_2$. Both $Y_{1a}$ and $Y_{1b}$ comprise three oligos, and their only difference is that they ligate to different ends of $Y_0$. This is done by using orthogonal ligation adapters.

$Y_0$ is the set of all tiles which can be ligated to $Y_1$, and $Y_N$ is the set of all tiles which can be ligated to $Y_{N-1}$ or to both $Y_{N-1}$ and $Y_{N+1}$ (at different ligation sites), where N is an integer greater than 0. Unique topologies can be designed by using orthogonal ligation adapters (as in $Y_{1a}$ and $Y_{1b}$), and/or by doing multi-step synthesis.

TIRF Imaging. A 12 lane PDMS chip with a liquid volume of 37.5 nL per lane (1.5 mm² area, 25 um height) was plasma treated and mounted on a #1 coverslip (Sigma-Aldrich). BSA-biotin (3 mg/mL) was used to biotinylate the glass surface. TE (+0.01% Tween 20, +100 mM NaCl, +10 mM MgCl2) was used 2×15 minutes for rinsing. Streptavidin (0.1 mg/mL) was used for 25 minutes, and then a 1×5 minute rinse in TE was done to wash out remaining streptavidin. An overnight static incubation of TE was done at room temperature. 1 uM biotinylated capture probe was added for 1.5 hours. A volume displacement of TE and a 4 hour TE static incubation was done to eliminate excess capture probe. Different *E. coli* total RNA concentrations were introduced to a complementary $Y_0$ reporter (labeled with two Cy3 fluorophores) at 1 nM for 15 minutes, and then introduced to the prepared lane for 4 hours. 3×1 hour static TE incubations were carried out to relieve background. TIRF was conducted with a 532 nm laser at 80 mW, with a 15 ms integration time on an ORCA-Flash 4.0.

Figure 6:
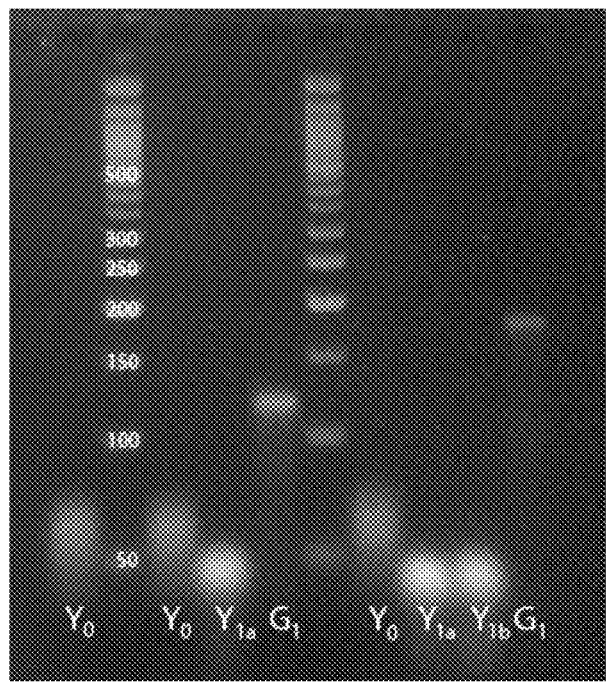
FIG. 6 depicts a demonstration of ligation control for G1 formation. The gel shown demonstrates G1 formation (3% agarose, SYBR Safe DNA Gel Stain). The two member G1 (on left) was assembled by ligating Y0 with Y¬1a, while the three member G1 was assembled by ligating Y0 with Y1a and Y1b.

FIG. 6 depicts a demonstration of ligation control for G1 formation. The gel shown demonstrates G1 formation (3% agarose, SYBR Safe DNA Gel Stain). The two member G1 (on left) was assembled by ligating Y0 with Y¬1a, while the three member G1 was assembled by ligating Y0 with Y1a and Y1b.

Figure 7:
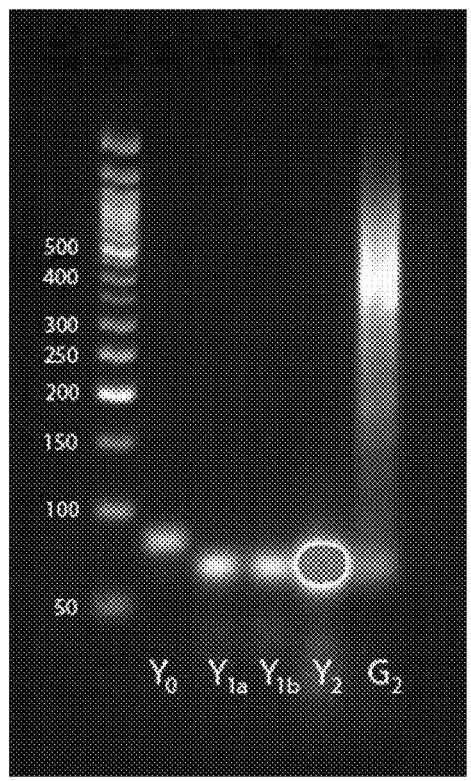
FIG. 7 depicts a one-step G2 synthesis. A seven tile G2 is formed when doing a one-step ligation reaction. The gel shown demonstrates G2 formation (3% agarose, SYBR Safe DNA Gel Stain). Incremental tiling is shown in the G2 well, where there are bands that go up to the complete product.

FIG. 7 depicts a one-step G2 synthesis. A seven tile G2 is formed when doing a one-step ligation reaction. The gel shown demonstrates G2 formation (3% agarose, SYBR Safe DNA Gel Stain). Incremental tiling is shown in the G2 well, where there are bands that go up to the complete product.

Figure 8:
FIG. 8 depicts a particle counting algorithm vs. image. *E. coli* total RNA was introduced to the prepared microfluidic device at 10 pg/uL. The original thresholded TIRF image is shown in white, while the MATLAB count output is shown in green. The two images were offset, and the resulting image displays proper counting.

FIG. 8 depicts a particle counting algorithm vs. image. *E. coli* total RNA was introduced to the prepared microfluidic device at 10 pg/uL. The original thresholded TIRF image is shown in white, while the MATLAB count output is shown in green. The two images were offset, and the resulting image displays proper counting.

Figure 9:
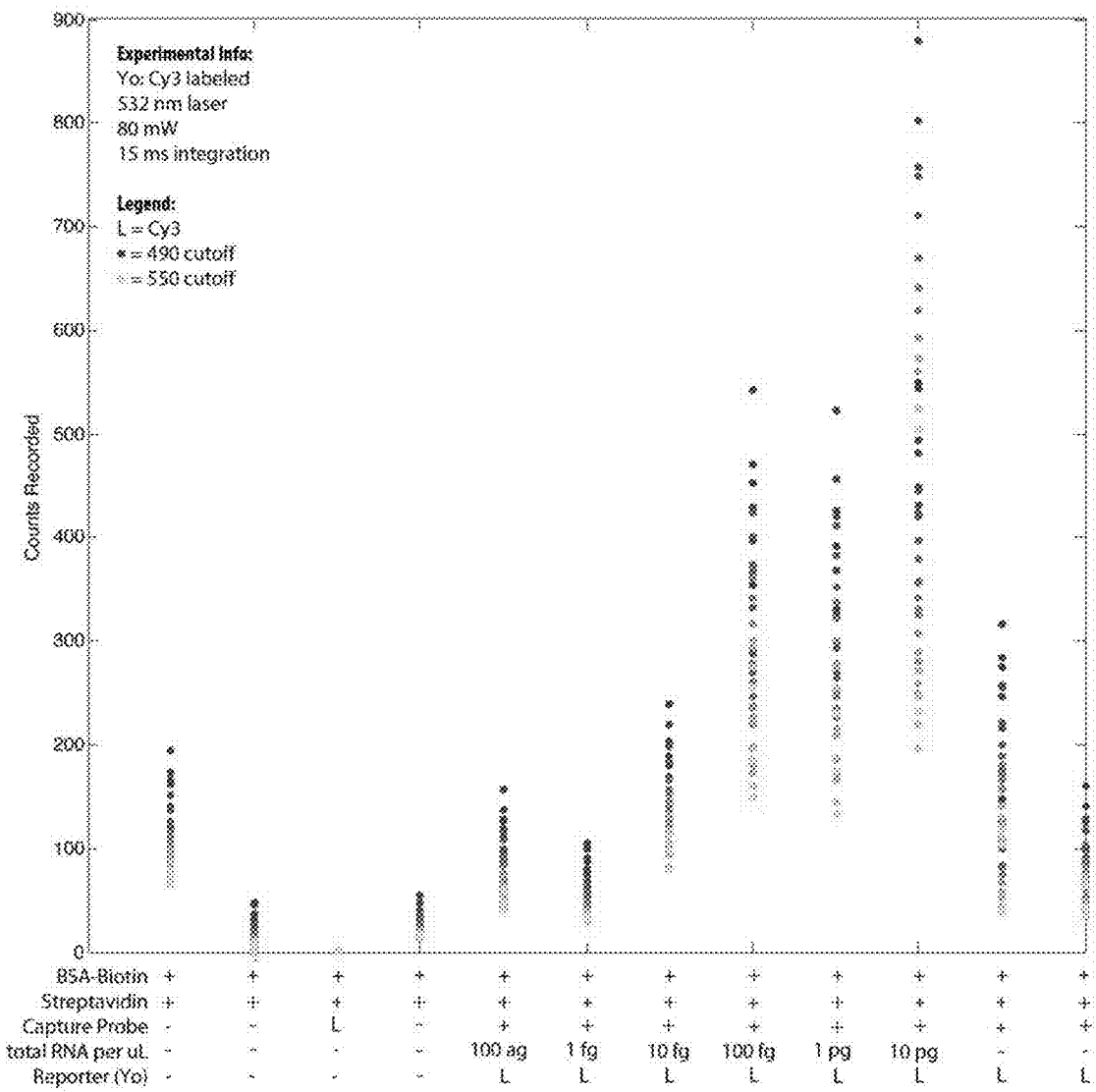
FIG. 9 depicts that *E. coli* total RNA titration shows trend in Cy3 counts (not background corrected). Counts are recorded as counts per field of view (TIRF, 60× magnification) and each condition corresponds to three images on one lane, which are each subjected to 10 thresholds. MATLAB was used to count spots that breach the specified thresholds. The images are not background corrected. The third lane, which serves as a positive control, is shown to only have one count. This is due to a fully saturated image, leading to one count (shown in FIG. 11A).

FIG. 9 depicts that *E. coli* total RNA titration shows trend in Cy3 counts (not background corrected). Counts are recorded as counts per field of view (TIRF, 60× magnification) and each condition corresponds to three images on one lane, which are each subjected to 10 thresholds. MATLAB was used to count spots that breach the specified thresholds. The images are not background corrected. The third lane, which serves as a positive control, is shown to only have one count. This is due to a fully saturated image, leading to one count (shown in FIG. 11A).

Figure 10:
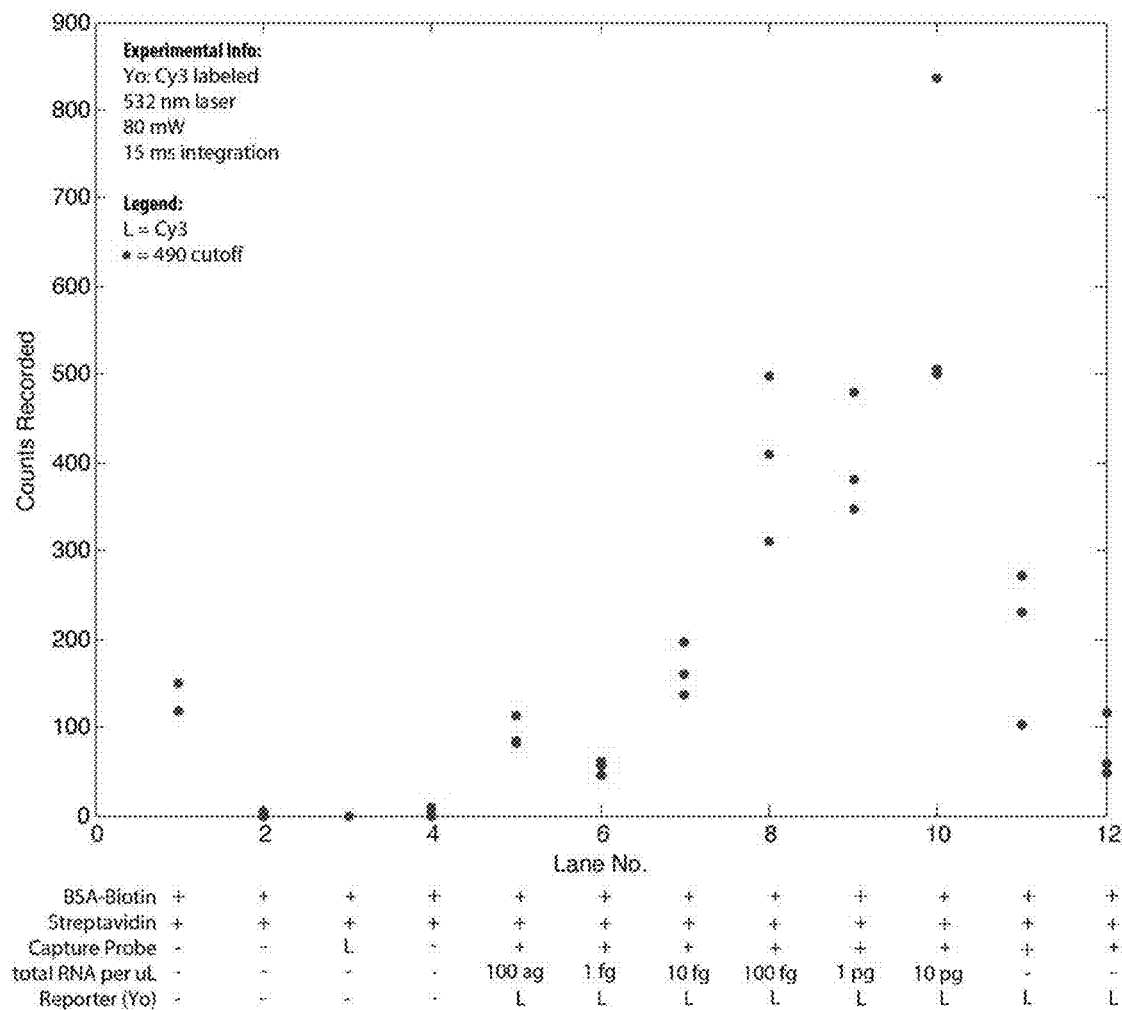
FIG. 10 depicts that *E. coli* total RNA titration shows trend in Cy3 counts (background corrected). Counts are recorded as counts per field of view (TIRF, 60× magnification) and each condition corresponds to three images on one lane. In the plot above, each condition was subjected to one threshold (pixel intensity >=490), and MATLAB was used to count spots that breach the specified threshold. The images are background corrected. The third lane, which serves as a positive control, is shown to only have one count. This is due to a fully saturated image, leading to one count (shown in FIG. 11A).

FIG. 10 depicts that *E. coli* total RNA titration shows trend in Cy3 counts (background corrected). Counts are recorded as counts per field of view (TIRF, 60× magnification) and each condition corresponds to three images on one lane. In the plot above, each condition was subjected to one threshold (pixel intensity >=490), and MATLAB was used to count spots that breach the specified threshold. The images are background corrected. The third lane, which serves as a positive control, is shown to only have one count. This is due to a fully saturated image, leading to one count (shown in FIG. 11A).

Figure 11A:
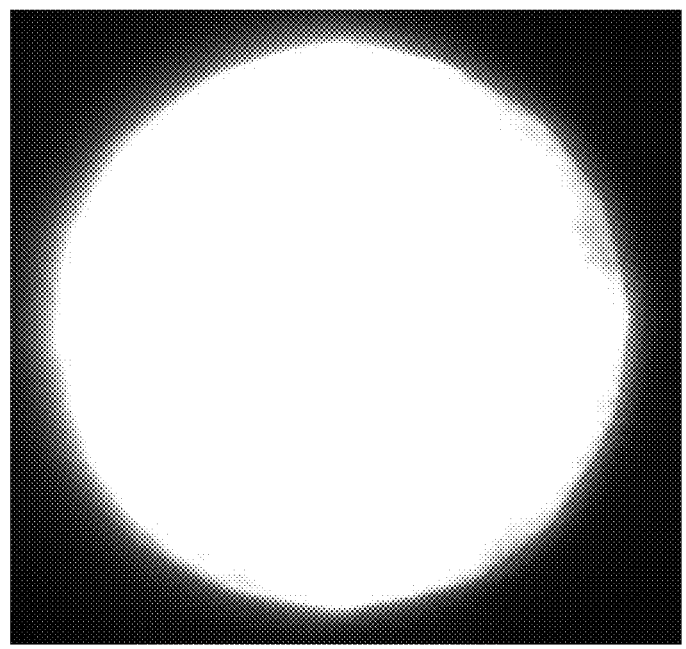
FIG. 11A depicts that a Cy3 labeled capture probe shows successful probe immobilization. This TIRF image corresponds to lane 3 in FIGS. 9 and 10, and shows a successful capture probe immobilization strategy. This image was taken with a 532 nm laser at 80 mW, and an integration time of 15 ms (60× magnification).

FIG. 11A depicts that a Cy3 labeled capture probe shows successful probe immobilization. This TIRF image corresponds to lane 3 in FIGS. 9 and 10, and shows a successful capture probe immobilization strategy. This image was taken with a 532 nm laser at 80 mW, and an integration time of 15 ms (60× magnification).

Figure 11B:
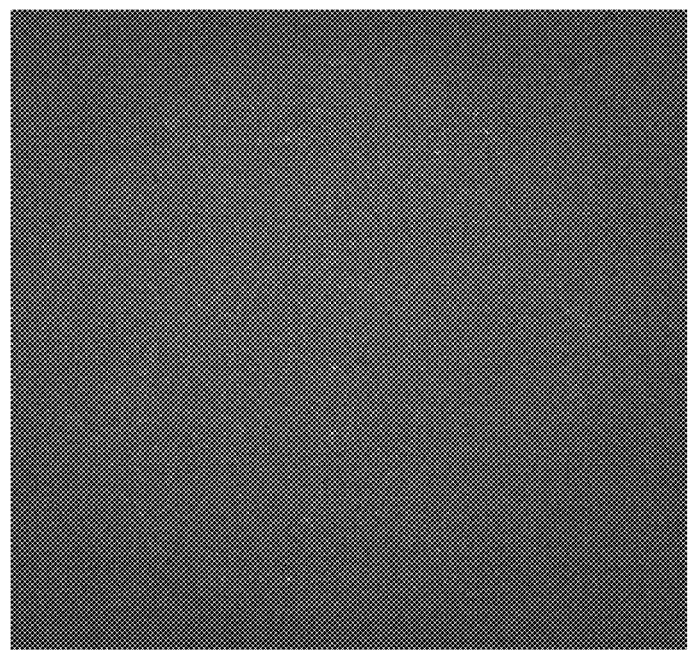
FIG. 11B depicts background counts (no Cy3). This TIRF image corresponds to lane 2 in FIGS. 9 and 10, and shows the background counts when Cy3 is not present. This image was taken with a 532 nm laser at 80 mW, and an integration time of 15 ms (60× magnification).

FIG. 11B depicts background counts (no Cy3). This TIRF image corresponds to lane 2 in FIGS. 9 and 10, and shows the background counts when Cy3 is not present. This image was taken with a 532 nm laser at 80 mW, and an integration time of 15 ms (60× magnification).

Figure 11C:
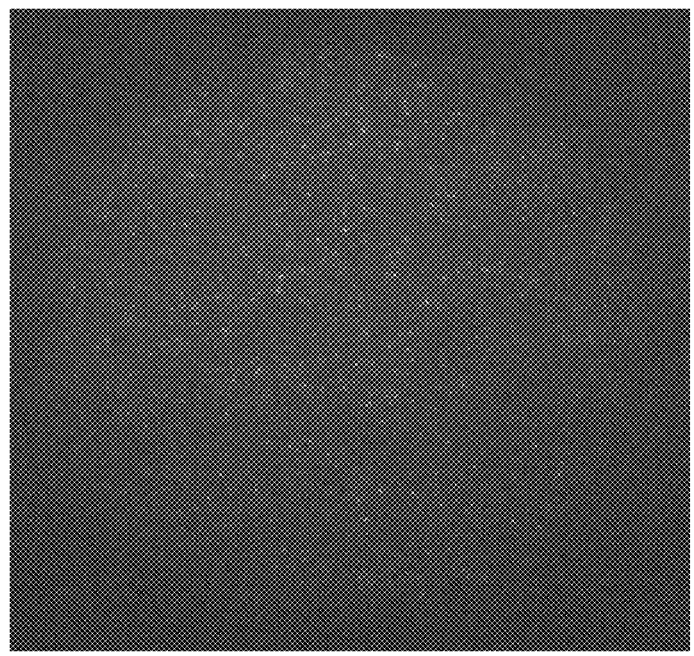
FIG. 11C depicts that 10 pg/uL of *E. coli* total RNA shows an increase in Cy3 counts. This TIRF image corresponds to lane 10 in FIGS. 9 and 10, and shows RNA-dependent counts. This image was taken with a 532 nm laser at 80 mW, and an integration time of 15 ms (60× magnification).

FIG. 11C depicts that 10 pg/uL of *E. coli* total RNA shows an increase in Cy3 counts. This TIRF image corresponds to lane 10 in FIGS. 9 and 10, and shows RNA-dependent counts. This image was taken with a 532 nm laser at 80 mW, and an integration time of 15 ms (60× magnification).

Figure 12:
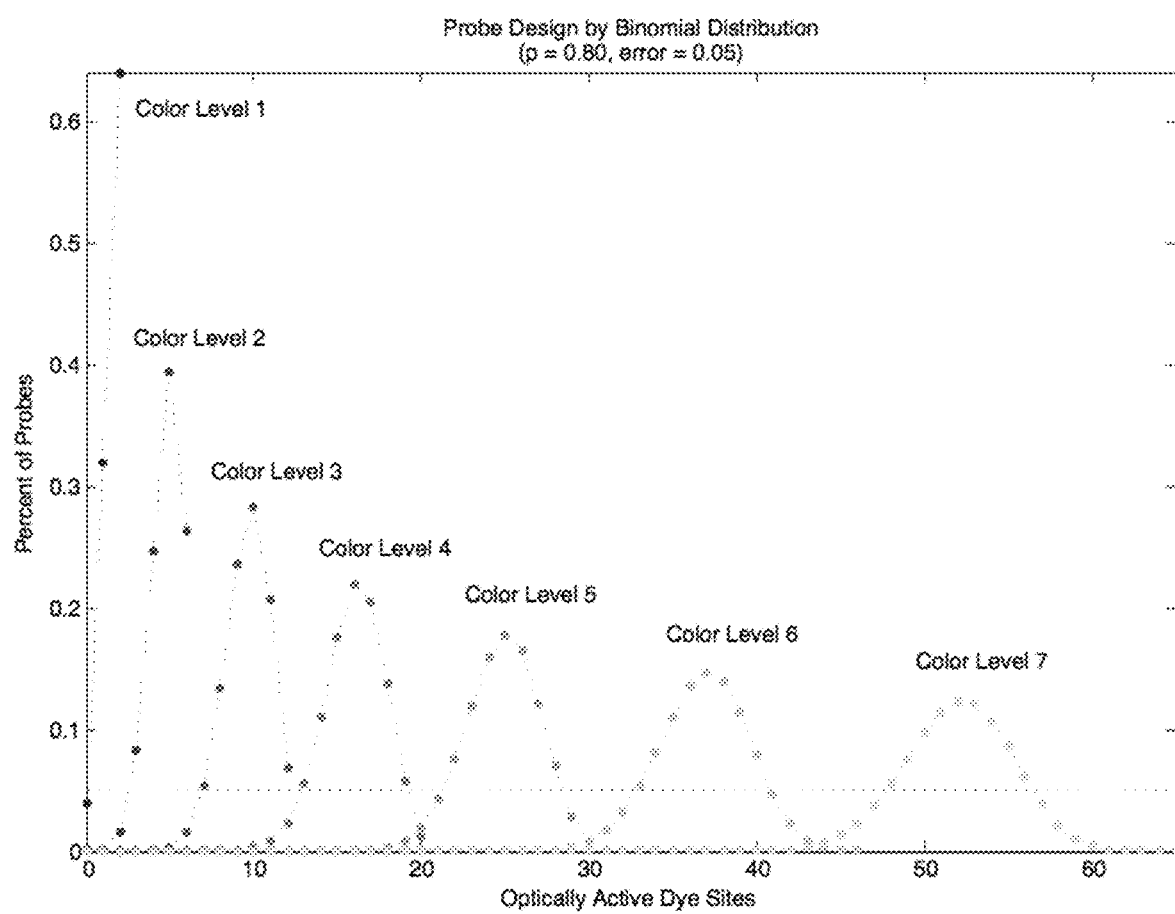
FIG. 12 depicts a probe design strategy. The distribution of optically active dyes in a reporter was calculated by the binomial distribution. By assuming a uniform probability of a dye being optically active (p), and by specifying the fraction of probes that are within the distribution of another color level (error) distributions can be selected such that color levels can be distinguished theoretically. These distributions correspond to an 80% chance (p=0.8) of a dye site being optically active, and a 5% overlap (error=0.05) between a color level distribution and the distribution of the preceding color level.

FIG. 12 depicts a probe design strategy. The distribution of optically active dyes in a reporter was calculated by the binomial distribution. By assuming a uniform probability of a dye being optically active (p), and by specifying the fraction of probes that are within the distribution of another color level (error) distributions can be selected such that color levels can be distinguished theoretically. These distributions correspond to an 80% chance (p=0.8) of a dye site being optically active, and a 5% overlap (error=0.05) between a color level distribution and the distribution of the preceding color level.

Figure 13:
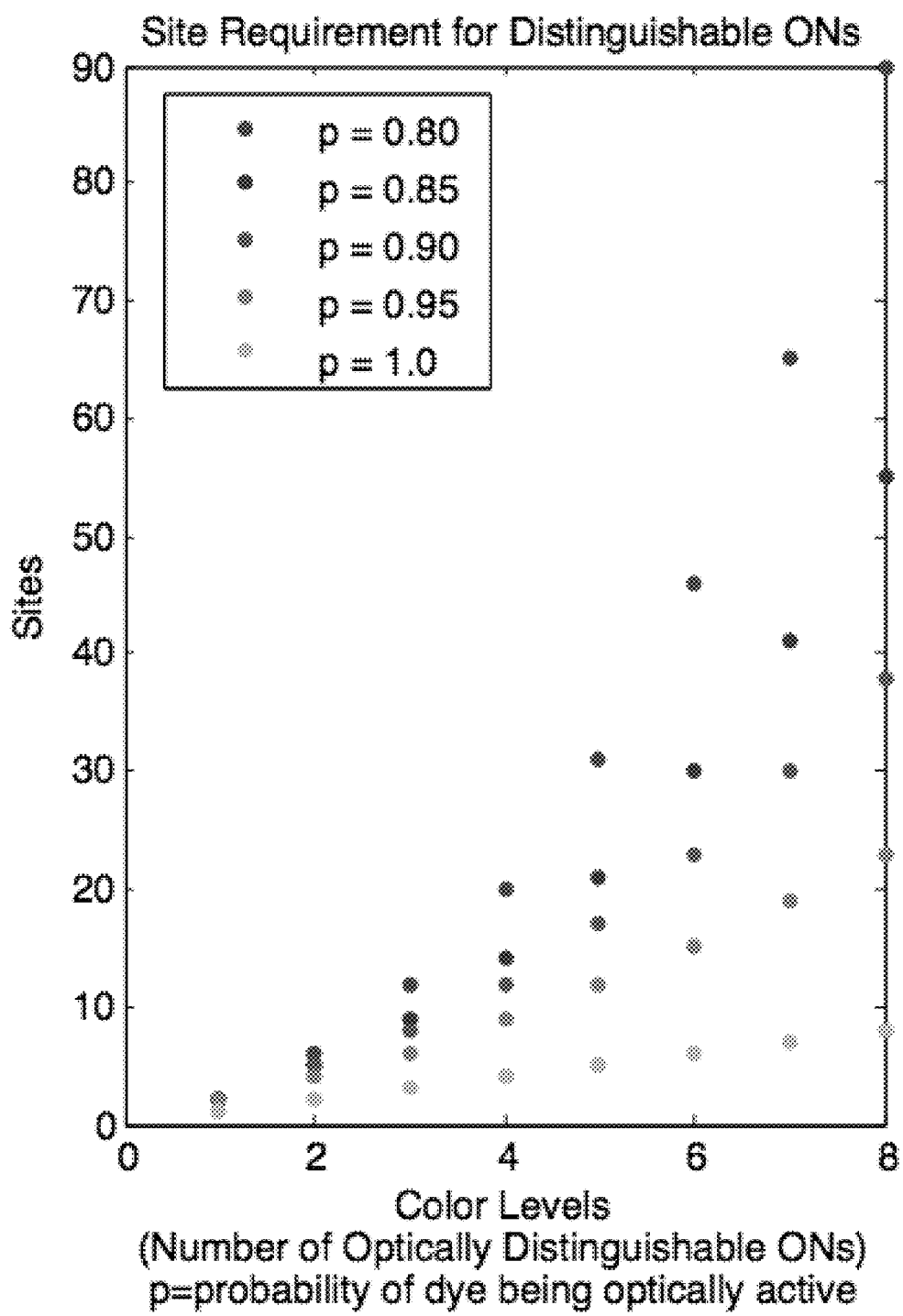
FIG. 13 depicts the number of sites required to achieve color level (distinguishable ON). The total dye site requirement in order to reach specified color levels is calculated by setting binomial distributions so that there is a maximum of a 5% overlap between the probability distribution of a color level and the probability distribution of the color level that precedes it (shown in FIG. 12). This shows the total dye sites that are required theoretically as a function of total color levels. As the probability of a dye being optically active increases, fewer sites are required in order to achieve theoretically distinguishable color levels.

FIG. 13 depicts sites required to achieve color level (distinguishable ON). The total dye site requirement in order to reach specified color levels is calculated by setting binomial distributions so that there is a maximum of a 5% overlap between the distributions of a color level and the color level that precedes it (shown in FIG. 12). This shows the total dye sites that are required theoretically as a function of total color levels. As the probability of a dye being optically active increases, fewer sites are required in order to achieve theoretically distinguishable color levels.

TABLE 1

Maximum Number of Distinguishable Reporters

| | | Maximum Colors | | |
|---|---|---|---|---|
| | | 1 | 2 | 3 |
| Maximum Color Levels | 1 | 1 | 3 | 7 |
| (Maximum Number of | 2 | 2 | 8 | 26 |
| Optically Distinguishable | 3 | 3 | 15 | 59 |
| ONs) | 4 | 4 | 23 | 89 |
| | 5 | 5 | 27 | 98 |
| | 6 | 0 | 0 | 0 |
| | 7 | 0 | 0 | 0 |

(tiles = 4, sites = 5, p = 0.8, error = 0.05)

Table 1 represents the cumulative amount of unique reporters available when applying a maximum number of available color levels, along with a maximum number of optically distinguishable ones. These calculations are reached when using 7 tiles, where each tile contains 5 sites for dye incorporation. Site availability is accounted for, and calculations are adjusted by assuming that 90% of dyes are optically active. Furthermore, a 5% error in probe identification is applied. FRET effects are ignored in this model.

TABLE 2A

Theoretical Maximum of Unique Reporters

| | | Maximum Colors | | |
|---|---|---|---|---|
| | | 1 | 2 | 3 |
| Maximum Color Levels | 1 | 1 | 3 | 7 |
| (Maximum Number of | 2 | 2 | 8 | 26 |
| Optically Distinguishable | 3 | 3 | 15 | 63 |
| ONs) | 4 | 4 | 24 | 124 |
| | 5 | 5 | 35 | 215 |
| | 6 | 0 | 0 | 0 |
| | 7 | 0 | 0 | 0 |

Reporters = (levels + 1)^colors − 1

Table 2A represents the cumulative amount of unique reporters available when applying a maximum number of available color levels, along with a maximum number of optically distinguishable Ons. Site availability is not accounted for.

TABLE 2B

Theoretical Yield %

| | | Maximum Colors | | |
|---|---|---|---|---|
| | | 1 | 2 | 3 |
| Maximum Color Levels | 1 | 100% | 100% | 100% |
| (Maximum Number of | 2 | 100% | 100% | 100% |
| Optically Distinguishable | 3 | 100% | 100% | 94% |
| ONs) | 4 | 100% | 96% | 72% |
| | 5 | 100% | 77% | 46% |
| | 6 | 0% | 0% | 0% |
| | 7 | 0% | 0% | 0% |

(Achievable/Unique) × 100%

TABLE 3

Maximum number of Distinguishable Reporters

| | | Maximum Colors | | |
|---|---|---|---|---|
| | | 1 | 2 | 3 |
| Maximum Color Levels (Maximum Number of Optically Distinguishable ONs) | 1 | 1 | 3 | 7 |
| | 2 | 2 | 8 | 26 |
| | 3 | 3 | 15 | 63 |
| | 4 | 4 | 24 | 123 |
| | 5 | 5 | 35 | 192 |
| | 6 | 6 | 45 | 237 |
| | 7 | 7 | 51 | 255 |

(tiles = 7, sites = 5, p = 0.9, error = 0.05)

Table 3 represents the cumulative amount of unique reporters available when applying a maximum number of available color levels, along with a maximum number of optically distinguishable Ons. These calculations are reached when using 7 tiles, where each tile contains 5 sites for dye incorporation. Site availability is accounted for, and calculations are adjusted by assuming that 90% of dyes are optically active. Furthermore, a 5% error in probe identification is applied. FRET effects are ignored in this model.

TABLE 4A

Theoretical Maximum of Unique Reporters

| | | Maximum Colors | | |
|---|---|---|---|---|
| | | 1 | 2 | 3 |
| Maximum Color Levels (Maximum Number of Optically Distinguishable ONs) | 1 | 1 | 3 | 7 |
| | 2 | 2 | 8 | 26 |
| | 3 | 3 | 15 | 63 |
| | 4 | 4 | 24 | 124 |
| | 5 | 5 | 35 | 215 |
| | 6 | 6 | 48 | 342 |
| | 7 | 7 | 63 | 511 |

Reporters = (levels + 1)^colors − 1

Table 4A represents the cumulative amount of unique reporters available when applying a maximum number of available color levels, along with a maximum number of optically distinguishable Ons. Site availability is not accounted for.

TABLE 4B

Theoretical Yield %
Theoretical Yield %

| | | Maximum Colors | | |
|---|---|---|---|---|
| | | 1 | 2 | 3 |
| Maximum Color Levels (Maximum Number of Optically Distinguishable ONs) | 1 | 100% | 100% | 100% |
| | 2 | 100% | 100% | 100% |
| | 3 | 100% | 100% | 100% |
| | 4 | 100% | 100% | 99% |
| | 5 | 100% | 100% | 89% |
| | 6 | 100% | 94% | 69% |
| | 7 | 100% | 81% | 50% |

(Achievable/Unique) × 100%

The invention is further described by the following numbered paragraphs:

1. A nucleic acid structure, comprising one or more nucleic acid tiles,
   (a) wherein each nucleic acid tile comprises nucleic acid oligomers, wherein each nucleic acid oligomer hybridizes to each other thereby forming a junction nucleic acid tile,
   (b) wherein each nucleic acid tile comprises two overhangs, wherein the two overhangs are overhangs A and B or overhangs A' and B', wherein A and A' are complementary overhangs and B and B' are complementary overhangs,
   (c) wherein at least one nucleic acid tile is labeled with a label and
   (d) wherein the one or more nucleic acid tiles are synthesized in a single step or by successive addition of nucleic acid tiles hybridizing at overhangs A and A' or B and B' thereby forming the nucleic acid structure comprising nucleic acid tiles.

2. The nucleic acid structure of paragraph 1 wherein one nucleic acid tile is labeled.

3. The nucleic acid structure of numbered paragraph 1 wherein two nucleic acid tiles are labeled.

4. The nucleic acid structure of numbered paragraph 1 wherein three nucleic acid tiles are labeled.

5. The nucleic acid structure of numbered paragraph 1 wherein four nucleic acid tiles are labeled.

6. The nucleic acid structure of numbered paragraph 1 wherein five nucleic acid tiles are labeled.

7. The nucleic acid structure of numbered paragraph 1 wherein six nucleic acid tiles are labeled.

8. The nucleic acid structure of numbered paragraph 1 wherein seven nucleic acid tiles are labeled.

9. The nucleic acid structure of any one of numbered paragraphs 1-8 wherein the nucleic acid structure comprises one, two, three, four, five, six or seven nucleic acid tiles.

10. The nucleic acid structure of any one of numbered paragraphs 1-9 wherein the nucleic acid tile is labeled with a single label, wherein each nucleic acid structure is distinguishable based upon a varying intensity of the label.

11. The nucleic acid structure of any one of numbered paragraphs 1-8 wherein the nucleic acid structure comprises fifteen nucleic acid tiles.

12. The nucleic acid structure of numbered paragraph 11 wherein the nucleic acid tile is labeled with one, two, three, four, five, six, seven, or eight labels wherein each nucleic acid structure is distinguishable based upon a varying intensity of the collection of labels.

13. The nucleic acid structure of any one of numbered paragraphs 1-8 wherein the nucleic acid structure comprises thirty-one nucleic acid tiles.

14. The nucleic acid structure of any one of numbered paragraphs 1-13 wherein the nucleic acid structure is labeled with 1, 2, 3, 4, 5, 6, 7, 8, 9, 10, 11, 12, 13, 14, 15, 16, 17, 18, 19 or 20 labels and/or combinations of different types of labels (such as red, green, and blue absorbing/emitting labels) wherein each nucleic acid structure is distinguishable based upon a varying properties or types of the labels or groups of labels, such as intensity, color, fluorescence lifetime, intensity variation, energy transfer, or photon statistics arising from photophysics of the labels.

15. The nucleic acid structure of any one of numbered paragraphs 1-14 wherein the label is a dye molecule, a fluorescent dye molecule, a quantum dot, a metal cluster, or a phosphorescent label.

16. The nucleic acid structure of numbered paragraph 15, wherein the fluorescent dye molecule is a terbium chelate derivative.

17. The nucleic acid structure of numbered paragraph 16, wherein the terbium chelate derivative is Cy3.

18. The nucleic acid structure of numbered paragraph 15, wherein the fluorescent dye molecule is fluorescein or rhodamine.

19. The nucleic acid structure of any one of numbered paragraphs 1-14 wherein the label is an organic label.

20. The nucleic acid structure of any one of numbered paragraphs 1-19 wherein the nucleic acid tile is a three way junction nucleic acid tile.

21. The nucleic acid structure of any one of numbered paragraphs 1-19 wherein the nucleic acid tile is a four way junction nucleic acid tile.

22. The nucleic acid structure of numbered paragraph 20 wherein in step (d) wherein $Y_0$ is a set of all tiles which are capable of being ligated to $Y_1$, and $Y_N$ is the set of all tiles which can be ligated to $Y_{N-1}$ or to both $Y_{N-1}$ and $Y_{N+1}$ (at different ligation sites), wherein N is an integer greater than 0.

23. The nucleic acid structure of numbered paragraph 22 wherein $Y_1$ ligates to $Y_0$.

24. The nucleic acid structure of numbered paragraph 22 or 23 wherein N=2 and $Y_2$ ligates to $Y_1$.

25. The nucleic acid structure of any one of numbered paragraphs 22-24, wherein $Y_1$ comprises $Y_{1a}$ and $Y_{1b}$, wherein $Y_{1a}$ and $Y_{1b}$ are both capable of being ligated to $Y_2$.

26. The nucleic acid structure of any one of numbered paragraphs 22-25, wherein $G_1$ comprises four three way junction nucleic acid tiles wherein each three way junction nucleic acid tile is $Y_0$, $Y_{1a}$, $Y_{1b}$, $Y_2$ or any combination thereof.

27. The nucleic acid structure of any one of numbered paragraphs 22-26, wherein $G_2$ comprises seven three way junction nucleic acid tiles.

28. The nucleic acid structure of any one of numbered paragraphs 1-27, wherein the nucleic acid structure is a nucleic acid dendrimer.

29. The nucleic acid structure of any one of numbered paragraphs 1-28, wherein the nucleic acid structure is a DNA structure.

30. A probe set comprising an optical probe comprising the nucleic acid structure of any one of numbered paragraphs 1-29, wherein the optical probe is conjugated to a hybridization probe, wherein the hybridization probe targets a nucleic acid.

31. A method of detecting a target nucleic acid sequence comprising adding the probe set of numbered paragraph 30 to a sample comprising the target nucleic acid sequence and identifying the target nucleic acid sequence bound to the probe set, wherein the identifying comprises detection of at least one label.

32. The method of numbered paragraph 31 wherein the detection of a label comprises measuring the intensity of the at least one label.

33. The method of numbered paragraph 31 or 32 further comprising photobleaching the at least one label.

34. The method of any one of numbered paragraphs 31-33 further comprising analyzing time-dependent intensity variations of the at least one label.

35. The method of any one of numbered paragraphs 31-34 further comprising measuring a duration of emission from the at least one label.

36. The method of any one of numbered paragraphs 31-35 wherein the target nucleic acid sequence is a stress response gene.

37. The method of numbered paragraph 36, further comprising exposing an organism comprising the stress response gene to an antibiotic and determining if the stress response gene is expressed.

38. The method of numbered paragraph 37, wherein the organism is a microbe.

39. The method of any one of numbered paragraphs 36 to 38, wherein the absence of a stress response gene indicates an antibiotic resistant organism.

40. The method of any one of numbered paragraphs 31-39 wherein the target nucleic acid originated in a human cell.

41. A microdevice comprising a tray accepting samples, antibiotics, and the signal/capture probe mixture, a microfluidics control module inside the microdevice, a cell concentration microdevice, a drug exposure and lysis microdevice, and a hybridization device with an optical system for fluorescence readout.

42. The microdevice of numbered paragraph 41 wherein the hybridization chip is mounted on a commercially available heating platform for temperature-controlled hybridization and wash steps, then moved in a single linear motion onto a printed receptacle that serves as a microscope stage.

43. The microdevice of numbered paragraph 41 or 42 wherein a light emitting diode array with optically-filtered LEDs in three colors, each of which tuned to excite one of the three colors in the optical barcode is above the stage.

44. The microdevice of any one of numbered paragraphs 41-43 wherein a 20× or 40× air objective on a focusing mount is beneath the stage.

45. The microdevice of any one of numbered paragraphs 40-44 further comprising a two-axis programmable translator with a spatial precision of 50 micron or better allows automatic scanning of the imaging area on the microdevice by moving it with respect to the fixed objective lens.

46. The microdevice of an one of numbered paragraphs 40-45 further comprising a motorized filter wheel in the emission path includes four positions, one to filter the emission of each color in the optical barcodes, plus a blank position for focus registration on fiducial marks in the sample (microfabricated features or beads randomly scattered in the imaging area) under low-intensity illumination.

47. The microdevice of any one of numbered paragraphs 40-46 further comprising a light collected by the objective lens is focused on a high-resolution, low noise, low speed, charge-coupled device array image sensor.

48. The microdevice of any one of numbered paragraphs 40-47 further comprising a laptop computer for recording an integration time image in the three color channels.

49. The microdevice of any one of numbered paragraphs 40-48 further comprising software for controlling the fluidics module, stage, focus mount, filter wheel, LED light source, and camera.

50. The microdevice of any one of claim 49 wherein the control systems and analysis algorithms sit behind a user interface that steps the user through sample and microdevice loading while verifying these steps have taken place by reading microswitch states.

51. Use of the microdevice of any one of claims 41-50 for extracting nucleic acids from a biological sample, such as a bodily fluid or laboratory sample.

52. Use of the microdevice of any one of numbered paragraphs 41-50 for mixing labeled nucleic acid structures with nucleic acids from the biological sample.

53. Use of the microdevice of any one of numbered paragraphs 41-50 wherein the device mixes the sample and probes in a small volume at high concentration to enable rapid reaction between the probes and sample nucleic acids.

54. Use of the microdevice of any one of numbered paragraphs 41-50 with surface chemistry recruiting probe-conjugated sample nucleic acid molecules to a surface to enable microscopy of the probe-sample molecular conjugates 55. Use of the microdevice of any one of numbered paragraphs 41-50 for integrating one, two, three, four, or all of the functions in numbered paragraphs 51-54.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A nucleic acid structure, comprising:
   (a) fifteen or more three-way junction DNA monomers assembled together, wherein each three-way junction DNA monomer comprises three or more hybridizing DNA strands and at least two overhangs:
      wherein the two overhangs are overhangs A and B or overhangs A' and B',
      wherein A and A' are complementary overhangs and B and B' are complementary overhangs;
      wherein at least one three-way junction DNA monomer is detectably labeled; and
      wherein the fifteen or more three-way junction DNA monomers are synthesized in a single step or by successive addition of three-way junction DNA monomers hybridizing at overhangs A and A' or B and B' thereby forming the nucleic acid structure comprising three-way junction DNA monomers;
   or
   (b) fifteen or more four-way junction DNA monomers assembled together, wherein each four-way junction DNA monomer comprises at least two overhangs,
      wherein the two overhangs are overhangs A and B or overhangs A' and B', wherein A and A' are complementary overhangs and B and B' are complementary overhangs,
      wherein at least one four-way junction DNA monomer is labeled with a label, and
      wherein the fifteen or more four-way junction DNA monomers are synthesized in a single step or by successive addition of four-way junction DNA monomers hybridizing at overhangs A and A' or B and B' thereby forming the nucleic acid structure comprising four-way junction DNA monomers.

2. The nucleic acid structure of claim 1,
   wherein each three-way or four-way-junction DNA monomer is labeled with a single label, wherein each nucleic acid structure is distinguishable based upon a varying intensity of the label or
   wherein the at least one three-way junction DNA monomer or the at least one four-way junction DNA monomer is labeled with one, two, three, four, five, six, seven, or eight labels wherein each nucleic acid structure is distinguishable based upon a varying intensity of the collection of labels or
   wherein the at least one nucleic acid structure is labeled with 1, 2, 3, 4, 5, 6, 7, 8, 9, 10, 11, 12, 13, 14, 15, 16, 17, 18, 19 or 20 labels and/or combinations of different types of labels.

3. The nucleic acid structure of claim 1, wherein the label is a dye molecule, a fluorescent dye molecule, a quantum dot, a metal cluster, or a phosphorescent label.

4. The nucleic acid structure of claim 3, wherein the fluorescent dye molecule is a terbium chelate derivative.

5. The nucleic acid structure of claim 4, wherein the terbium chelate derivative is Cy3.

6. The nucleic acid structure of claim 3, wherein the fluorescent dye molecule is fluorescein or rhodamine.

7. The nucleic acid structure of claim 1, wherein the label is an organic label.

8. The nucleic acid structure of claim 1 wherein $Y_0$ is a set of all three-way or four-way junction DNA monomers which are capable of being ligated to $Y_1$, wherein $Y_1$ is $Y_N$ when N=1, and $Y_N$ is the set of all DNA monomers which can be ligated to $Y_{N-1}$ or to both $Y_{N-1}$ and $Y_{N+1}$ (at different ligation sites), wherein N is an integer greater than 0.

9. The nucleic acid structure of claim 8,
   wherein $Y_1$ ligates to $Y_0$ or
   wherein N=2 and $Y_2$ ligates to $Y_1$ or
   wherein $Y_1$ comprises $Y_{1a}$ and $Y_{1b}$, wherein $Y_{1a}$ and $Y_{1b}$ are both capable of being ligated to $Y_2$ or
   wherein the nucleic acid structure comprises four three-way or four-way junction DNA monomers wherein each three-way or four-way junction DNA monomer is $Y_0$, $Y_{1a}$, $Y_{1b}$, $Y_2$ or any combination thereof or
   wherein the nucleic acid structure comprises seven three-way or four-way junction DNA monomers.

10. The nucleic acid structure of claim 1,
    wherein the nucleic acid structure is a nucleic acid dendrimer or
    wherein the nucleic acid structure is a DNA structure.

11. A probe set comprising an optical probe comprising the nucleic acid structure of claim 1, wherein the optical probe is conjugated to a hybridization probe, wherein the hybridization probe targets a nucleic acid.

12. A method of detecting a target nucleic acid sequence comprising adding the probe set of claim 11, to a sample comprising the target nucleic acid sequence and identifying the target nucleic acid sequence bound to the probe set, wherein the identifying comprises detection of at least one label.

13. The method of claim 12,
    wherein the detection of a label comprises measuring the intensity of the at least one label or
    further comprising photobleaching the at least one label or
    further comprising analyzing time-dependent intensity variations of the at least one label or
    further comprising measuring a duration of emission from the at least one label.

14. The method of claim 12, wherein the target nucleic acid sequence is a stress response gene.

15. The method of claim 14, further comprising exposing an organism comprising the stress response gene to an antibiotic and determining if the stress response gene is expressed.

16. The method of claim 15, wherein the organism is a microbe.

17. The method of claim 14, wherein the absence of a stress response gene indicates an antibiotic resistant organism.

18. The method of claim 12, wherein the target nucleic acid originated in a human cell.

* * * * *